(12) United States Patent
Planelles et al.

(10) Patent No.: US 7,973,018 B2
(45) Date of Patent: Jul. 5, 2011

(54) CELL CYCLE ARREST AND APOPTOSIS

(75) Inventors: Vicente Planelles, Salt Lake City, UT (US); Joshua L. Andersen, Sandy, UT (US); Erik Zimmerman, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 83 days.

(21) Appl. No.: 11/665,416

(22) PCT Filed: Oct. 21, 2004

(86) PCT No.: PCT/US2004/035464
§ 371 (c)(1),
(2), (4) Date: Aug. 13, 2008

(87) PCT Pub. No.: WO2006/046951
PCT Pub. Date: May 4, 2006

(65) Prior Publication Data
US 2008/0300201 A1    Dec. 4, 2008

(51) Int. Cl.
*A61K 48/00* (2006.01)
*A61K 35/00* (2006.01)
(52) U.S. Cl. .......................................... 514/44; 424/93.1
(58) Field of Classification Search ........................ None
See application file for complete search history.

(56) References Cited

PUBLICATIONS

Xu et al. Cancer Biology 1996, vol. 7, pp. 33-40.*
Bano in AIDS, 2007, vol. 21, No. 13, pp. 1829-1836.*
Anderson et al., ATR and GADD45alpha mediate HIV-1 Vpr-induced Apoptosis, Cell Death Differentiation, Apr. 2005, pp. 326-334, vol. 79, No. 17, Nature Publishing Group.
Kolonin et al., Reversal of Obesity by Targeted Ablation of Adipose Tissue, Nature Medicine, Jun. 2004, pp. 625-632, vol. 10, No. 6.
Muthumani et al., Adenovirus encoding HIV-1 Vpr activates caspase 9 and induces apoptotic Cell Death in Both p53 positive and negatvce Human Tumor Cell Lines, Oncogene, pp. 4613-4625, 2002, Nature Publishing Group.
Roshal et al., Activation of the ATR-mediated DNA Damage Response by the HIV-1 Viral Protein R, Journal of Biological Chemistry, Jul. 2003, pp. 25879-25886, vol. 278, No. 28.
Yoshizuka et al., Human Immunodeficiency Virus Type 1 Vpr-Dependent Cell Cycle Arrest Through a Mitogen-Activated protein Kinase Signal Transduction pathway, Journal of Virology, Sep. 2005, pp. 11366-11381, vol. 79, No. 17.
Zimmerman et al., Human Immunodeficiency Virus Type 1 Vpr-Mediated G2 Arrest Requires Rad17 and Huas and Induces Nuclear BRCA1 and gemma-H2AX Focus Formation, Molecular and Cellular Biology, pp. 9289-9294, Nov. 2004, vol. 24, No. 21.
International Search Report and Written Opinion, PCT/US04/35464, dated Jul. 28, 2006.

\* cited by examiner

*Primary Examiner* — Bao Li
(74) *Attorney, Agent, or Firm* — Ballard Spahr LLP

(57) ABSTRACT

The HIV-1 accessory gene vpr encodes a conserved 96-amino acid protein that is necessary and sufficient for the HIV-1-induced block of cellular proliferation and induction of apoptosis. Expression of vpr in CD4+ lymphocytes results in G2 arrest, followed by apoptosis. ATR, as a cellular factor that mediates Vpr-induced cell cycle arrest, is required for activation of the Breast Cancer-Associated Protein-1 (BRCA1). In addition, the Growth Arrest and DNA Damage protein (GADD45) is upregulated by Vpr in an ATR-dependent manner. Posttranscriptional silencing of either ATR or GADD45 leads to nearly complete suppression of the pro-apoptotic and/or cell cycle arrest effect of Vpr.

7 Claims, 11 Drawing Sheets

CELL CYCLE ARREST AND APOPTOSIS

STATEMENT REGARDING FEDERALLY SPONSORED RESEARCH OR DEVELOPMENT

Work described herein was supported in part by National Institute of Health Grant Nos. AI49057 and AI054188. The United States Government may have certain rights in the invention.

TECHNICAL FIELD

This invention relates generally to biotechnology, more particularly, to compounds, compositions, and/or methods useful in the regulation of apoptosis and/or $G_2$ cell cycle arrest.

BACKGROUND

Human immunodeficiency virus type 1 (HIV-1) has four genes, vif, vpr, vpu, and nef; termed "accessory genes," that are dispensable for viral replication ill vitro (14). Many important functions related to HIV-1 pathogenesis have been ascribed to these accessory genes. Specifically, Vpr has been implicated in long terminal repeat transactivation, nuclear import of the preintegration complex, induction of $G_2$ cell cycle arrest, and apoptosis. Recent studies identifying single amino acid changes in Vpr in a cohort of HIV-1-infected long-term nonprogressors substantiated the role of Vpr in HIV-1 pathogenesis in vivo (29, 43). Vpr induces $G_2$ arrest and apoptosis in infected CD4+ lymphocytes (18, 21, 35, 38). $G_2$ arrest by Vpr is effected in HeLa cells through activation of the ATR-dependent DNA damage checkpoint pathway (40). This data supports previous work demonstrating the inhibition of cyclin B1-p34$^{cdc2}$ complexes by Vpr (18) and establishes the identity of some of the upstream regulators of Cdc2. ATR-dependent activation of Chk1 kinase leads to the inhibition of Cdc25C phosphatase, which is normally required to dephosphorylate and activate Cdc2 (40). The signaling pathway downstream of ATR activation was recently reviewed in references 1 and 33.

While Vpr activates the ATR-specific checkpoint, the role of other molecules required in the ATR pathway is not known. Activated ATR can also phosphorylate proteins other than those required for $G_2$ arrest. One of these substrates is the histone 2A variant X (H2AX). H2AX is deposited randomly throughout chromatin, comprising approximately 10% of total nucleosomal histone H2A (34). H2AX has a highly conserved serine residue at position 139 that is phosphorylated by ATR and/or ATM in response to DNA damage (10, 37, 46). It is estimated that hundreds to thousands of H2AX molecules are phosphorylated per double-stranded break (37). ATM-dependent H2AX phosphorylation occurs in response to doublestranded DNA breaks (10, 46, 47). In contrast, ATR phosphorylates H2AX under circumstances of replication stress, such as stalled replication forks (9). In the presence of DNA damage or replication stress, H2AX molecules that are located in the vicinity of the DNA lesion become phosphorylated in a highly specific localized manner (34). Thus, immunofluorescence staining for phosphorylated H2AX (also referred to as γ-H2AX) following DNA damage produces a staining pattern of distinct nuclear foci (34). γ-H2AX is thought to amplify the DNA damage signal by enhancing and stabilizing the recruitment of DNA damage sensor proteins, such as ATR, ATM, Rad17, and the 9-1-1 complex, and DNA repair proteins, such as breast cancer susceptibility protein 1 (BRCA1), Nbs1, Mre11, and Rad50, to sites of DNA damage (15). This action may effectively "mark" the site of DNA damage, maintaining checkpoint signaling at the damaged region until DNA repair is completed.

Another substrate of activated ATR is BRCA1. BRCA1 is important for both checkpoint activation and DNA repair. BRCA1 colocalizes with DNA repair factors, such as Rad51, PCNA, and Mre11-Rad50-Nbs1 (15). It has been proposed that BRCA1 may represent an essential link in coordinating cell cycle arrest with genomic repair efforts (reviewed in reference 27) and with the induction of apoptosis.

In addition to a role in cell cycle arrest, Vpr plays a role in apoptosis. However, it is not possible to extrapolate the findings relating to cell cycle arrest to apoptosis, as the pathways do not completely overlap or follow one from the other. Therefore, there is also a need to determine the role of Vpr in apoptosis.

It has been suggested that apoptosis of infected cells may play a significant role in the depletion of CD4+ lymphocytes in vivo (62, 82, 56, 93). However, the mechanism by which Vpr induces apoptosis was not understood. Muthumani et al. reported that vpr-expressing cells undergo apoptosis via the intrinsic pathway that involves loss of mitochondrial membrane potential (74). This pathway of apoptosis is characterized by cytochrome C release, and caspase 9 activation, and is triggered in the absence of death receptor ligation (74). However, the initial event induced by Vpr towards activation of the proapoptotic signaling cascade was not elucidated.

To elucidate whether Vpr might directly promote the release of pro-apoptotic mediators from the mitochondria, Veira et al., and Jacotot et al. incubated recombinant Vpr with purified mitochondria (88, 67). These two studies found that in a cell-free system, Vpr interacts with the permeability transition pore complex (PTPC) to cause ion permeability and swelling of mitochondria leading to release of cytochrome C (88, 67). These results support a model in which Vpr induces mitochondrial depolarization directly rather than activating upstream stress signals (88, 67). The present invention provides data that does not support the model of Jacotot et al. and provides additional methods of activating apoptosis.

DISCLOSURE OF THE INVENTION

The invention relates to the induction of apoptosis and/or cell cycle arrest in a subject. The invention also relates to the induction of apoptosis and/or cell cycle arrest in a subject lacking one or more functional ATR, BRAC1, RAD17 and/or GADD45 proteins. For example, the invention relates to the treatment of breast cancer by introducing Vpr and BRAC1, or a functional fragment thereof, into a breast cancer cell having a mutation in BRAC1, wherein Vpr and BRAC1 induce apoptosis in a cancer cell.

Another aspect of the invention relates to one or more Vectors containing one or more Vpr, ATR, BRAC1, RAD17, HUS1 or GADD45 encoding nucleic acid sequences. The nucleic acid in the vector can be operatively linked to a promoter, for example, an inducible or regulatable promoter that is capable of expressing or overexpressing a protein, such as Vpr, ATR, BRAC1, RAD17, HUS1 and/or GADD45, or that is capable of expressing or overexpressing the protein in a conditional manner. The vector may include one or more of the following: a selectable marker, an origin of replication, or other sequences known in the art, The nucleic acid encoding a protein such as Vpr, ATR, BRAC1, RAD17, HUS1 and/or GADD45, or a vector including such a nucleic acid, may be contained in a cell, such as a bacterial, mammalian, or yeast cell. Another aspect of the invention relates to host cells containing a vector capable of directing expression of a protein, such as Vpr, ATR, BRAC1, RAD17, HUS1 and/or GADD45.

The invention also relates to a method of increasing apoptosis and/or $G_2$ cell cycle arrest in a subject, such as a cancer cell, by introducing one or more nucleic acid sequences encoding one or more Vpr, AIR, BRAC1, RAD17, HUS1 or GADD45 proteins.

The invention also relates to a compound comprising Vpr or a functional fragment thereof linked to a tissue targeting moiety, such as an adipose tissue targeting moiety. For example, the targeting moiety of SEQ ID NO: 1.

The invention also relates to a method of treating obesity in a subject, wherein Vpr linked to a targeting moiety is administered to the subject.

The invention also relates to a method of inducing apoptosis in a subject by introducing Vpr and BRAC1 and/or ATR, or a functional fragment thereof to the subject and inducing apoptosis. The subject is optionally believed to suffer from breast cancer due to a mutation in a brac1 gene or a subject having a mutation in an atr gene. In another aspect, the invention relates to a method of inducing GADD45 by administering Vpr, ATR, or a functional fragment thereof, to the subject.

The invention also relates to a method of inducing G2 cell cycle arrest by administering Vpr, activated ATR, or a functional fragment thereof to a subject, inducing activation of BRAC1, HUS1 and/or RAD17, and arresting cell cycle progression in G2.

The invention also relates to a method of screening a compound for apoptotic activity, comprising administering a compound to a subject having an ATR protein and a BRAC1 protein, assaying for ATR dependent phosphorylation of BRAC1, and identifying the compound as inducing or inhibiting apoptosis. Optionally, ATR dependent phosphorylation of BRAC1 comprises assaying for phosphorylation at serine 1423 of BRAC1. Optionally, Vpr may be introduced into the subject. As will be recognized by a person of ordinary skill in the art, introducing a protein includes introducing a nucleic acid encoding the protein as well as introducing the protein itself.

Optionally, the methods of the invention may comprise knocking down ATR ATR, BRAC1, RAD17 and/or GADD45 expression in a subject.

The invention also relates to a medicament and/or method of manufacturing a medicament for the treatment of a disease in a subject.

BRIEF DESCRIPTION OF THE DRAWINGS

FIG. 1A is an immunoblot of total Rad17 (upper panel) or actin (lower panel). Cells were mock transfected (lane 1), transfected with nonspecific siRNA (lane 2), or transfected with Rad17-specific siRNA (lane 3). FIG. 1B illustrates the results of cell cycle analysis of HeLa cells transfected as indicated, and infected with lentivirus vector pHR-Vpr or pHR-GFP. Cell cycle distributions were analyzed 48 h after infection. Left peaks represent diploid cells in G1. Right peaks represent tetraploid cells in G2/M.

FIGS. 3A and 3B show HeLa cells that were transduced with lentivirus vector pHR-Vpr or pHR-GFP, mock transduced, or treated with 10 mM HU for 2 h, at 48 h after transduction, cells were stained with γ-H2AX- or BRCA1-specific antibodies and visualized for γ-H2AX (red) (3A) or BRCA1 (red) (3B) and GFP (green) localization by confocal microscopy. FIG. 3C illustrates γ-H2AX- and BRCA1-positive and -negative cells that were visually counted. Results represent averages for three fields with approximately 50 cells per field. FIG. 3D shows human primary thymocytes that were infected with HIV-1NL4-3 (bottom panel) or mock infected (top panel) and, at 20 h postinfection, fixed and stained for γ-H2AX.

FIG. 4A illustrates an immunoblot of total ATM (upper panel), ATR (middle panel), or actin (lower panel). Cells were mock transfected (lane 1) or transfected with nonspecific siRNA (lane 2), ATM-specific siRNA (lane 3), or ATR-specific siRNA (lane 4). FIG. 4B illustrates cell cycle analysis of HeLa cells transfected as indicated and infected with lentivirus vector pHR-Vpr or pHR-GFP. Cell cycle distributions were analyzed at 48 h after infection. Left peaks represent diploid cells in G1. Right peaks represent tetraploid cells in G2/M.

FIG. 6. siRNA-mediated knockdown of ATR and GADD45 abrogates Vpr-induced apoptosis.

BEST MODES FOR CARRYING OUT THE INVENTION

As used herein, "peptide," "polypeptide" and "protein" include polymers of two or more amino acids of any length. No distinction, based on length, is intended between a peptide, a polypeptide or a protein.

In addition to initiating $G_2$ arrest signaling through Chk1, activated ATR also phosphorylates cellular proteins in separate branches of the DNA damage response (see, Table 1). ATR is a 2,644 amino acid protein with a C-terminal catalytic domain, which is flanked by two loosely conserved domains In light of the fact that ATR has at least eight cellular targets for phosphorylation (1, 51), additional pathways controlled by ATR may be affected by Vpr-dependent activation. *Therefore, the activation status of other known ATR targets has been investigated. The present invention shows that both Rad17 and Hus1 are required for Vpr-mediated $G_2$ arrest.* In addition, HIV-1 Vpr expression leads to the formation of intense γ-H2AX and BRCA1 nuclear foci, characteristic markers of DNA damage. These results suggest a role of Vpr in activating the ATR-dependent $G_2$ checkpoint. However, other aspects of HIV-1 pathogenesis, such as the induction of apoptosis, remain speculative, at best, based on this data alone.

Rad17 is a replication factor C-related protein that, in a complex with Rfc2, Rfc3, Rfc4, and Rfc5, loads the heterotrimeric sliding clamp consisting of Rad9, Rad1, and Hus1 (9-1-1 complex) at sites of DNA damage (54). ATR, Rad17, and the 9-1-1 complex colocalize and activate one another to signal $G_2$ checkpoint activation (54). Rad17 and the 9-1-1 complex are necessary for downstream signaling of $G_2$ arrest through ATR activation (54).

Figure 5:
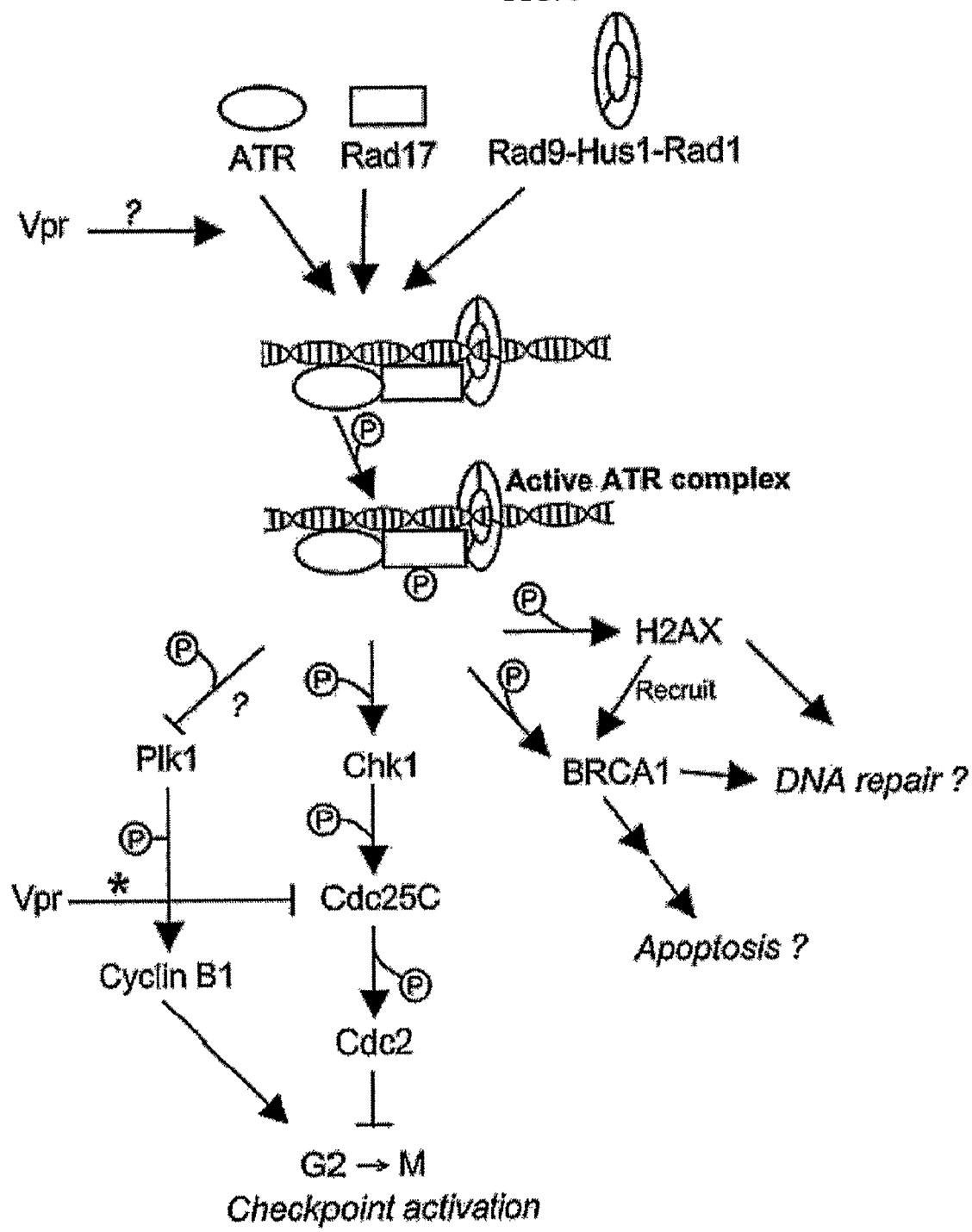
FIG. 5 shows a schematic representation of the ATR pathway. ATR has eight known targets; only the ones with potential relevance to HIV-1 Vpr are represented. Question marks denote functional relationships that are expected but not confirmed. The asterisk denotes the inhibition of Cdc25C reported by Goh et al. (17).

It is shown here that Vpr activates ATR and its downstream signaling events in a manner that is similar to that of activation by bona fide DNA damage (FIG. 5 shows a schematic diagram). Various means of genetic analysis, including, RNA interference, knockout cell lines, and/or dominant-negative constructs, may be used to demonstrate Vpr-dependent activation of $G_2$ arrest and apoptosis. Important mechanistic details of the downstream signaling consequences are now being elucidated.

Rad17 and Hus1 are required for signaling when ATR dependent $G_2$ arrest is induced in response to genotoxic stress. Upon recognition of genotoxic stress, Rad17 is phosphorylated and is the first target of ATR (54) (FIG. 5). This phosphorylation requires the participation of Hus1 (and the larger complex of which Hus1 is a part, 9-1-1) (54). Only after Rad17 is phosphorylated can ATR modify its next target, Chk1. By down-regulating endogenous Rad17 protein levels via RNA interference, the present invention shows that Rad17 function is also required for Vpr-induced $G_2$ arrest. Additionally, the present invention shows that Hus1-deficient cells are refractory to the effects of Vpr on the cell cycle. Therefore, Rad17 and Hus1 are necessary components of the $G_2$ checkpoint response to Vpr expression.

Interestingly, Hus1 is known to be dispensable for ATR mediated H2AX phosphorylation (46). Based on these findings, Ward and Chen (46) suggested that ATR activation may lead to two types of downstream events, which are Hus1 dependent and Hus1 independent. Hus1-dependent consequences of ATR activation (such as Chk1 phosphorylation) may specifically induce cell cycle arrest, while downstream events independent of Hus1 (such as H2AX phosphorylation) may recruit members of the DNA repair machinery, such as BRCA1, Nbs1, and Rad50 (15, 46).

Figure 2:
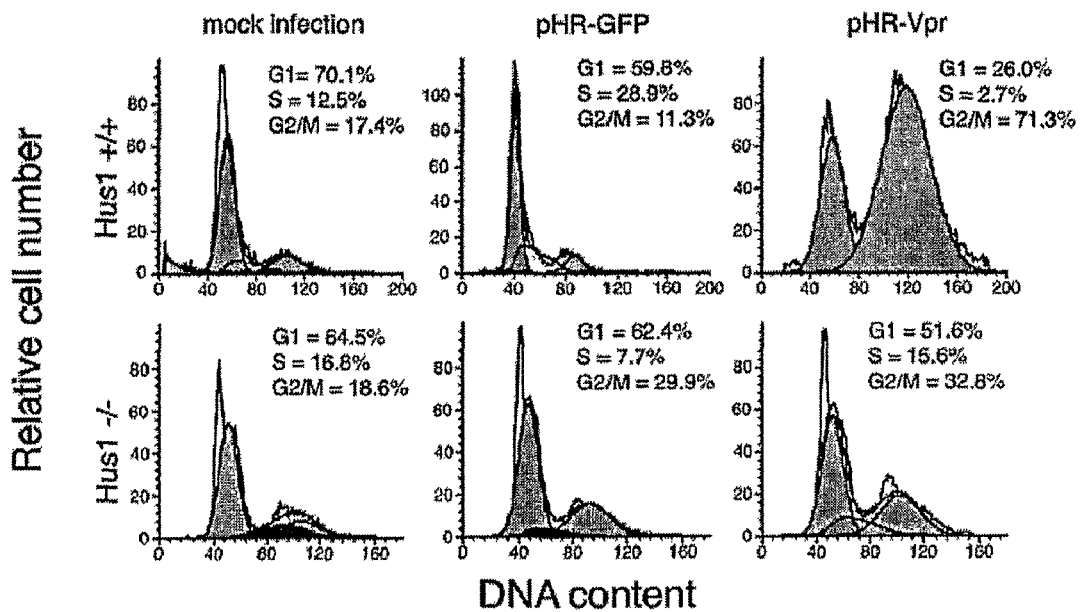
FIG. 2. Hus1 is required for Vpr-mediated G2 arrest. Hus1$^{-/-}$ p21$^{-/-}$ or Hus1$^{+/+}$ p21$^{-/-}$ mouse embryonic fibroblasts were infected with lentivirus vector pHR-Vpr or pHR-GFP. Cell cycle distributions were analyzed at 48 h after infection.

The cyclin-dependent kinase inhibitor $p21^{Waf1}$ was previously shown to be transcriptionally upregulated in a p53-dependent fashion in the context of Vpr expression (12). This observation led the authors to formulate the hypothesis that $p21^{Waf1}$ may mediate Vpr-induced $G_2$ arrest, although this hypothesis was not tested (12). Here it is shown that $p21^{Waf1-/-}$ mouse embryonic fibroblasts are able to activate the $G_2$ checkpoint when transfected with Vpr (FIG. 2). Without wishing to be bound by theory, this observation suggests that $p21^{Waf1}$ does not play a major role in mediating $G_2$ arrest by Vpr.

It is shown here that Vpr induces γ-H2AX and BRCA1 focus formation. Therefore, four targets of ATR that have been tested (Table 1) play an active role in the response to Vpr expression. Due to the present observation of a very specific histone modification and directed recruitment of a known DNA repair protein in response to Vpr, it is believed that Vpr-induced ATR stimulation occurs at distinct sites throughout chromatin. This specificity may be due to DNA sequence, chromatin modifications, or replication- and expression-dependent DNA and/or chromatin dynamics. Vpr-induced signaling through ATR may have cellular effects other than $G_2$ arrest, such as recruitment of DNA repair proteins and/or initiation of apoptotic signaling cascades.

TABLE 1

Phosphorylation targets of ATR and their roles in activation of the $G_2$ checkpoint

| ATR target (reference) | Status in the presence of Vpr (reference or source)a |
|---|---|
| Chk1 (25) | P, A (40) |
| Rad17 (54) | N (this work) |
| H2AX (9, 10, 37, 46) | P, F (this work) |
| BRCA1 (45) | P, F (this work) |
| Plk1 (13) | ? |
| p53 (24) | D (41) |

TABLE 1-continued

Phosphorylation targets of ATR and their roles in activation of the $G_2$ checkpoint

| ATR target (reference) | Status in the presence of Vpr (reference or source)a |
|---|---|
| 53BP1 (46, 48) | ? |
| E2F (11, 36) | ? | a: P, phosphorylated; A, activated; N, necessary for G2 checkpoint activation; F, focus formation; ?, unknown; D, dispensable for $G_2$ checkpoint activation.

The present invention demonstrates that primary human CD4+ thymocytes, an in vivo target for HIV-1 (22, 23), display γ-H2AX foci when infected with full-length HIV-1. Therefore, the findings with HeLa cells can be extended to primary CD4+ cells, one of the target cell types of HIV-1. More importantly, this indicates that the host cell DNA damage response is activated in the context of an HIV-1 infection.

These results may also be replicated in natural targets of HIV-1 (such as primary CD4+ lymphocytes and macrophages). However, human primary cells that are defective for genes in the ATR pathway are rare or nonexistent. Hence, RNA interference technology with primary cells may be used to test the necessity of various mediators for activation of the $G_2$ checkpoint by Vpr. Although transfection of primary cells with RNA duplexes is inefficient, construction of lentivirus vectors expressing short hairpin RNAs (5, 6) offer an additional alternative or sorting of the cell population based on co-transfection of a selection or sorting marker.

The polo-like kinase (Plk1) has been described as a positive regulator of the $G_2$/M transition. This effect is thought to be mediated by Plk1 kinase activity directed at cyclin B1 (13). Plk1 phosphorylation promotes nuclear accumulation of the cyclin B1-Cdc2 heterodimer, ultimately allowing progression into M phase (26). In instances of DNA damage, Plk1 kinase activity is inhibited to prevent advance into mitosis (FIG. 5) (42). It has been demonstrated that this inhibition is dependent on the kinase activity of ATR (13). Thus, inactivation of Cdc25C by Chk1 may not be the sole contributor to inducing $G_2$ arrest, and concerted action by Plk1 may also be required.

The p53-binding protein, 53BP1, rapidly associates with nuclear foci containing γ-H2AX, ATR, and BRCA1 in response to genotoxic stress (7, 46). This organization into foci occurs in an ATR-dependent manner in response to replication stress (46, 48). If Vpr directly causes DNA lesions, stalls replication forks to cause double-stranded breaks, or somehow mimics DNA damage through DNA, chromatin, or protein-protein interactions, then one would expect 53BP1 to be activated by ATR.

The transcriptional activator E2F1 is another target of ATR. E2F1 is essential for promoting the $G_1$/S transition and DNA replication. E2F1 is also involved in several stress response pathways, including apoptosis and DNA repair (reviewed in references 11 and 36). For example, E2F1 is implicated in p53-dependent apoptosis in response to DNA damage (19, 39). It has also been shown that E2F1 recruits the DNA repair proteins Nbs1 and Mre11 to origins of replication (30). Therefore, E2F1 phosphorylation may play a role in the cellular response to Vpr.

The tumor suppressor p53 can be a target for ATR as well as for ATM, leading to the induction of cell cycle arrest and apoptosis in response to environmental insults, including DNA damage (reviewed in reference 24). Shostak et al. previously examined the role of p53 in mediating the effects of Vpr and found that p53 is dispensable for both checkpoint activation and apoptosis induction (41). However, it is possible that the activation of p53 by ATR may allow Vpr to modulate certain aspects of infected cells via the transcriptional effects of p53. For example, p53 is known to transcriptionally activate the p53-dependent ribonucleotide reductase, p53R2, thrombospondin-1, and aldehyde dehydrogenase-4, enzymes which participate in diverse processes, such as DNA repair, inhibition of angiogenesis, and the response to oxidative stress, respectively (for a review, see reference 31).

The precise mechanism of ATR activation in the context of HIV-1 Vpr has remained unclear (FIG. 5). ATR activation is thought to be specific for DNA damage manifested as single-stranded DNA through either processed double-stranded breaks or stalled replication forks due to either replicational pausing or single-stranded breaks; in contrast, the ATM response is thought to be predominantly responsible for the immediate signaling of unprocessed double-stranded DNA breaks (1, 33). This pathway specificity suggests that Vpr activates the DNA damage-induced $G_2$ checkpoint in a manner that resembles or causes the accumulation of single-stranded DNA. Therefore, there are several possible mechanisms by which Vpr may activate ATR. One possibility is that Vpr directly causes DNA lesions through intrinsic nuclease activity. This possibility seems unlikely, as Vpr shares no sequence homology or known structural motifs with any known nucleases. Another plausible explanation is that Vpr inappropriately recruits ATR or other DNA damage-sensing proteins to undamaged DNA through DNA-protein and protein-protein interactions. Alternatively, Vpr could interact with proteins or DNA in a manner that causes DNA damage. One possible mode of indirectly inducing DNA damage would be the recruitment of an endonuclease which would enzymatically induce single-stranded or double-stranded DNA breaks which, once processed into single-stranded DNA, would activate ATR.

Vpr may also interact with DNA or proteins present at sites of DNA replication in a manner that inhibits replication fork progression. It has been proposed that abnormally long, replication protein A-bound single-stranded DNA at stalled replication forks allows for ATR recruitment via an ATR-interacting protein (55). Additionally, if halted forks are not stabilized and resolved, then their eventual collapse can activate DNA damage sensors (1, 33). However, if this were a highly potent, nonspecific effect of Vpr, then one would expect a global inhibition of replication manifested as early S-phase arrest, instead of the conspicuous $G_2$ arrest. Vpr could directly interact with DNA in a fashion that causes or resembles damaged DNA or stalled replication forks. It has been shown that the C-terminal alpha helix of Vpr binds DNA in vitro and that Vpr is detected in chromatin and nuclear matrix fractions in vivo (28, 52).

An alternative model suggests that Vpr may directly interact with ATR or other components of the checkpoint signaling pathway independent of DNA or chromatin localization. Coprecipitation experiments for ATR and Vpr using conventional methods have been unable to demonstrate any binding between these proteins. However, the use of cross-linking agents to stabilize a potentially weak interaction or a protein complex with multiple proteins bridging ATR and Vpr may demonstrate interaction.

A recent study indicated that Vpr interacts directly with Cdc25C and inhibits Cdc25C phosphatase activity (17). Inhibition of Cdc25C then prevents activation of the cyclin B1-p34$^{cdc2}$ complex. Although this finding does not explain why ATR, Rad17, Hus1, and Chk1 are required for Vpr-induced $G_2$ arrest (FIG. 5), it is plausible that Vpr induces $G_2$ arrest in a redundant manner, both by signaling DNA damage and by inhibiting downstream mediators of cell cycle progression, such as Cdc25C (17). It is also formally possible that Cdc25C inhibition has an unforeseen effect on the activation or expression of upstream proteins in the ATR signaling cascade. Regardless of the mechanism of action, Vpr is shown to induce $G_2$ arrest and may be used to induce such an arrest in target cells. For example, Vpr or a functional fragment thereof may be introduced into cancer cells or a subject to produce a desired $G_2$ arrest.

The cytopathic effects of HIV-1 infection are thought to be multiple and related to the expression of several viral genes. The present invention demonstrates that Vpr has at least two discrete functions, it exerts a potent antiproliferative effect due to $G_2$ arrest and also produces proapoptotic effects. However, the interrelationship of $G_2$ arrest and apoptosis is not clear, since Rad17 is important for checkpoint activation and BRCA1 is related to DNA damage and may be potentially proapoptotic (FIG. 5).

Since Vpr was found to be sufficient to induce apoptosis (86), the functional relationship between induction of apoptosis and that of $G_2$ arrest has been controversial. While G2 arrest plateaus at approximately 36 hours post-transduction with pHR vectors, apoptosis appears to be maximal at 48-72 hours. In addition, alleviation of cell cycle arrest with drugs such as caffeine largely eliminated induction of apoptosis (5). On the other hand, mutants of Vpr have been described, which are able to partially dissociate both phenotypes (89, 75, 29, 43). The present invention provides a different model, where $G_2$ arrest and apoptosis are induced concomitantly, since both are dependent on activation of the same kinase, ATR. However, for reasons that were not understood, apoptosis and $G_2$ arrest develop with different kinetics, such that $G_2$ arrest peaks first. Without wishing to be bound by theory, two different targets of ATR may initiate the $G_2$ arrest and apoptotic responses. These targets are believed to be CHK1 and BRCA1/GADD45, respectively. In support of this model, the data demonstrates that siRNA-mediated knockdown of ATR effectively abrogates both responses.

The present invention demonstrates that, in contrast to the studies by Veira et al. and Jacotot et al. (67, 88), the treatment of vpr-infected cells with caffeine, which inhibits the DNA damage-signaling proteins ATM and ATR, significantly reduces Vpr-induced apoptosis (53). This observation indicates that Vpr first induces stress signals that are similar or identical to those induced by certain forms of genotoxic stress, and then these signals activate a proapoptotic signaling cascade. It has recently been found that ATR is the mediator of Vpr-induced DNA damage-like signals (40). It was reasoned that if Vpr induces apoptosis by directly binding and controlling the PTPC, then signaling through ATR would still be necessary for induction of $G_2$ arrest, but would be dispensable for induction of apoptosis. Conversely, if ATR activation was required for induction of apoptosis, then examination of potential pro-apoptotic phosphorylation targets of ATR should identify a specific target or set of targets that would mediate the signaling events between ATR activation and apoptosis.

ATR targets initiate signaling cascades that may result in three global effects: cell cycle blockade, recruitment of DNA repair/transcription factors, and induction of apoptosis. The present invention shows that both RAD17 and H2AX are targets of Vpr. Because p53 has been previously ruled out as a mediator of apoptosis induced by Vpr (41, 87), another possible pro-apoptotic target of ATR, BRCA1 was examined.

In response to genotoxic insults, BRCA1 is recruited to sites of DNA damage and is phosphorylated by both ATM and ATR (45, 58). BRCA1 has been proposed to play a distinct role in DNA repair and apoptosis as a transcriptional regulator of genes including Cyclin B1, p53R2, MDM2, and p53 (72). Recently, GADD45 was identified as a transcriptional target of BRCA1 (65).

GADD45 was originally identified in Chinese hamster cell lines as one of several genes rapidly induced by UV radiation (61). GADD45 is induced by a variety of genotoxic stresses including ionizing radiation (IR), medium starvation, and methyl methanesulfonate (MMS) (69, 78), and has been shown to play roles in both $G_2$/M arrest and apoptosis following DNA damage (68, 94). Harkin et al. demonstrated that BRCA1-induced upregulation of GADD45 resulted in JNK/SAPK-dependent apoptosis (65). In the present invention, targets of ATR with possible roles in Vpr-induced apoptosis were examined and Vpr-induced apoptosis was found to be signaled through the DNA damage signaling protein ATR, which initiates a pathway that involves activation of BRCA1 and upregulation of GADD45. Hence, both ATR and GADD45 are required for Vpr-induced apoptosis.

Loss of $CD4^+$ lymphocytes over the course of an HIV-1 infection plays a central role in disease progression and immune suppression in AIDS patients (reviewed in ref. (66)). However, the mechanism by which $CD4^+$ T cells are lost is poorly understood. Several mechanisms have been proposed to explain the loss of $CD4^+$ T cells in HIV-1-infected patients, including direct killing by HIV-1 infection, $CD8^+$ T cell-mediated killing of infected $CD4^+$ lymphocytes, and apoptosis of uninfected "bystander" cells. In addition, the HIV-1 proteins Tat, Rev, Vpu, Nef and Vpr have been implicated in the apoptosis of infected and/or bystander cells (reviewed in ref. (79)).

Previous reports have demonstrated in vitro binding of Vpr to the PTPC, which resulted in the release of cytochrome C from fractionated mitochondria (88, 67). These observations suggest that Vpr induces mitochondrial depolarization directly rather than activating upstream stress receptors, such as ATR. However, the model proposed by Jacotot et al. does not explain the observation that Vpr-expressing cells undergo apoptosis in a cell cycle-dependent manner, specifically from $G_2$. The observations of Jacotot et al. would also suggest that Vpr induces apoptosis rapidly after being expressed (67), in contrast, observations made with virus infection indicate that apoptosis induced by Vpr is maximal at day 3 post-infection.

The present invention demonstrates that Vpr induces formation of distinct BRCA1 foci within the nucleus of vpr-expressing cells, concomitant with Vpr-induced apoptosis and $G_2$ arrest. Vpr also induces ATR-dependent phosphorylation of BRCA1 at serine 1423, which is indicative of BRCA1 activation following genotxic stress (45). It has been suggested that BRCA1 plays a role in transcriptional regulation of genes involved in cell cycle arrest, apoptosis, and DNA repair (71, 72). Specifically, overexpression of BRCA1 resulted in transcriptional upregulation of GADD45 (65, 72). Data presented herein shows that activation of BRCA1 is concomitant with upregulation of GADD45. Upregulation of GADD45, by Vpr, may require BRCA1, which is tested by knockdown of BRAC1 or use of $BRAC1^{-/-}$ subjects. BRCA1 C-terminus acts as a transactivation domain that has been suggested to play a critical role in cancer development.

Interestingly, upregulation of GADD45 by Vpr does not result in activation of the MAP Kinases p38 or JNK (65, 73). In the context of reports from Harkin et al. demonstrating that overexpressed BRCA1 results in GADD45 upregulation and JNK-dependent apoptosis (65), the present results suggest that a JNK- and p38-independent pathway is active in Vpr-induced apoptosis. Wang et al. demonstrated that GADD45-deficient fibroblasts are capable of JNK activation following DNA damage, and wild-type fibroblasts, in response to UV radiation, showed JNK activation prior to GADD45 upregulation (90). These data suggest that the proapoptotic effects of GADD45 may be signaled by a pathway that circumvents activation of the MAP Kinases, p38 and JNK. GADD45 is able to associate with several other proteins, including p21$^{Waf1}$, CDC2, and the proliferating subject nuclear antigen (PCNA) (57, 70, 83, 94). These GADD45 partners are assayed for a role in apoptosis induced by Vpr.

RNAi

The RNAi pathway consists of the presentation of a "triggering" dsRNA that is subsequently processed into siRNAs by an RNaseIII-like enzyme, for example, Dicer (Zamore, P. D. et al., *RNAi: double-stranded RNA directs the ATP-dependent cleavage of in RNA at 21 to 25 nucleotide intervals*, 101 Cell 25 (2000); Hutvagner, G. and Zamore, P. D., *RNAi: nature abhors a double-strand*, 12 Curr. Opin. Genet. Dev. 225 (2002)). This siRNA species, which may be about 19 to about 25 bp in length, is then incorporated into a multi-subunit RNA-induced silencing complex, which targets the unique cellular RNA transcript for enzymatic degradation. RNA hydrolysis occurs within the region of homology directed by the original siRNA (Fibashir, S. M. et al., *RNA interference is mediated by 21 and 22 nucleotide RNAs*, 15 Genes Dev. 188 (2001)), thereby selectively inhibiting target gene expression.

dsRNA activates a normal cellular process leading to a highly specific RNA degradation, and a cell-to-cell spreading of this gene silencing effect in several RNAi models. (Shuey, et al, *RNAi: gene-silencing in therapeutic intervention*, 7(20) Drug Discovery Today 1040 (2002)). Injection of dsRNA, for example, acts systemically to cause post-transcriptional depletion of the homologous endogenous RNA in *C. elegans* (U.S. Pat. Appl. Pub. No. 2003/0084471 A1). This depletion of endogenous RNA causes effects similar to a conditional gene 'knock out,' revealing the phenotype caused by the lack of a particular gene function. *C. elegans* nematodes can, for example, be fed with bacteria engineered to express dsRNA corresponding to a *C. elegans* target gene. Nematodes fed with engineered bacteria show a phenotype similar to mutants containing a mutation in the target gene (1998 Nature 395: 854). Likewise, RNAi may be used in other subjects.

To circumvent the limitations of transfection efficiency, while retaining desirable sustained RNAi expression, a selection marker may be incorporated. This method allows for the selection of cells having the RNAi molecule, using the selection marker to sort such cells. Briefly, the method comprises introducing an RNAi molecule or molecule capable of producing the RNAi and a selection marker or molecule capable of producing the selection marker, and sorting the cells based on the presence of the separation marker. Hence, such RNAi technology may be used to enrich a population of cells transfected with RNAi, such as BRAC1 RNAi, and the selectable marker, thereby compensating for low transfection efficiency.

Proteins and/or peptides disclosed herein may be synthesized using D-amino acids or other amino acid modifications known in the art. For example, Vpr may be produced using one or more D-amino acids to reduce proteolysis and/or degradation.

Those skilled in the field of molecular biology will understand that any of a wide variety of expression systems may be used to provide a recombinant protein or protein fragment. The methods of transformation, transfection or transduction, and the choice of expression vehicle (vector), will depend on the host system selected. Transformation and transfection methods are described, e.g., in Ausubel, F. M. et al. (eds) (1997) CURRENT PROTOCOLS IN MOLECULAR BIOLOGY, John Wiley & Sons.; expression vehicles may be chosen from those provided, for example, in Cloning Vectors: A Laboratory Manual (P. H. Pouwels et al., 1985, Supp. 1987) or known in the art.

Constructs of the invention may be prepared for introduction into a prokaryotic or eukaryotic host and may comprise a replication system recognized by the host, including the intended polynucleotide fragment encoding the desired polypeptide, and will preferably also include transcription and translational initiation regulatory sequences operably linked to the polypeptide encoding segment. The choice of vector will often depend on the host cell into which it is to be introduced. Thus, the vector may be an autonomously replicating vector, a viral or phage vector, a transposable element, an integrating vector or an extrachromosomal element, such as a minichromosome or an artificial chromosome. Such vectors may be prepared by means of standard recombinant techniques well known in the art. See for example, see Ausubel (1992); Sambrook and Russell (2001); and U.S. Pat. No. 5,837,492.

The proteins of the invention may be cotranslationally, post-translationally or spontaneously modified, for example, by acetylation, farnesylation, glycosylation, myristoylation, methylation, prenylation, phosphorylation, palmitoylation, sulfation, ubiquitination and the like. See, Wold, F. (1981), Annu. Rev. Biochem. 50:783-814.

The present invention allows for the treatment of cancer, for example, familial breast cancer, by introducing Vpr and BRAC1, or a functional fragment thereof, into such a subject having or thought to have ATR activity. Since the absence of ATR prevents activation of BRAC1 and is required for Vpr-induced apoptosis, the invention allows for the treatment of cancerous cells lacking one or more of the functional forms of a required proteins. As will be evident to a person of skill in the art in light of the present invention, the disease state and known or postulated mutations may be appropriately matched to the proteins disclosed herein and the treatment tailored to the particular disease. Hence, the invention provides a method of treating a cancerous cell lacking ATR, RAD17, HUS1, BRAC1 and/or GADD45 function by introducing Vpr and the appropriate protein, or a functional fragment thereof, into the cancerous cell, thereby inducing G2 cell cycle arrest and/or apoptosis.

Obesity is an increasingly prevalent human condition and, although recent progress has been made in understanding the underlying mechanism, no safe and effective treatment exists on the market. The present invention provides a compound and/or method of inducing GADD45 and/or activating BRAC1 in adipose tissue or adipose tissue supporting vasculature of a subject, comprising a targeting motif, such as a CKGGRAYDC (SEQ ID NO:1) peptide and/or one or more peptides as disclosed in U.S. Patent Publication 20040170955, published Sep. 2, 2004, linked to Vpr and/or a functional fragment of Vpr, wherein a functional fragment is a fragment capable of activating BRAC1 and/or inducing GADD45 in a subject. In another embodiment, a method of activating BRAC1 and/or inducing GADD45 is provided, wherein Vpr or a functional fragment thereof is administered to a subject.

Other tissue targeting moieties include, but are not limited to, a molecule which is bound by a receptor and transported into a cell by a receptor-mediated process, such as glucose, galactose, mannose, mannose 6-phosphate, transferrin, asialoglycoprotein, α-2-macroglobulins; insulin, a peptide growth factor, cobalamin, folic acid or derivatives, biotin or derivatives, YEE(GalNAcAH)$_3$ or derivatives, albumin, texaphyrin, metallotexaphyrin, porphyrin, any vitamin, any coenzyme, an antibody, an antibody fragment (e.g., Fab) and a single chain antibody variable region (scFv), cobalamin and/ or cobalamin analogues or derivatives. For example, studies have shown that the absorption of physiological amounts of vitamin B12 by the gut requires that it be complexed with a naturally occurring transport protein known as intrinsic factor (IF). (Castle, 1953; Fox and Castle, Allen and Majerus. 1972b). Folic acid, folinic acid, pteropolyglutamic acid, and folate receptor-binding pteridines such as tetrahydropterins, dihydrofolates, tetrahydrofolates and their deaza and dideaza analogs are useful as targeting molecules in accordance with the present invention. The terms "deaza" and "dideaza" analogs refer to the art-recognized analogs having a carbon atom substituted for one or two nitrogen atoms in the naturally-occurring folic acid structure. For example, the deaza, analogs include the 1-deaza, 3-deaza, 5-deaza, 8-deaza, and 10-deaza analogs. The dideaza analogs include, for example, 1,5-dideaza, 5,10-dideaza, 8,10-dideaza, and 5,8-dideaza analogs. The foregoing folic acid derivatives are conventionally termed "folates," reflecting their capacity to bind with folate-receptors, and such ligands when complexed with exogenous molecules are effective to enhance trans-membrane transport. Other folates useful as complex forming ligands for this invention are the folate receptor binding analogs aminopterin, amethopterin (methotrexate). $N^{10}$-methylfolate, 2-deamino-hydroxyfolate, deaza analogs such as 1-deazamethopterin or 3-deazamethopterin, and 3'5'-dichloro4-amino-4-deoxy-$N^{10}$-methylpteroyl-glutamic acid (dichloromethotrexate). In addition, biotin analogs such as biocytin, biotin sulfoxide, oxybiotin and other biotin receptor-binding compounds are ligands that may also be used as suitable targeting molecules to promote the trans-membrane transport of exogenous molecules, such as the proteins described herein. Other suitable ligands capable of binding to receptors to initiate receptor-mediated endocytotic transport of the complex include anti-idiotypic antibodies to the folate receptor. An exogenous molecule in complex with an anti-idiotypic antibody to a receptor is used to trigger trans-membrane transport of the complex. Such molecules are used in accordance with the present invention as a targeting molecule (see, U.S. Pat. No. 6,315,978). Any of these targeting moieties may be linked to a protein or functional fragment thereof, such as Vpr, ATR, RAD17, HUS1, BRAC1, GADD45, thereby allowing the targeting of the protein or functional fragment thereof to a desired cell type.

Linker molecules are known in the art and include, but are not limited to, organic molecules, such as one or more amino acids or other hydrocarbon chains, or one or more carbohydrate molecules, such a sugar unit, which may be modified such that the modified sugar and/or linker is resistant to cleavage. The sugars of a linker may be modified by methods known in the art, for example, to achieve resistance to nuclease cleavage. Examples of modified sugars include, but are not limited to, 2'-O-alkyl riboses, such as 2'-O-methyl ribose, and 2'-O-allyl ribose. The sugar units may be joined by phosphate linkers. The linker may comprise a hydrogen, and/or a straight or branched, substituted or unsubstituted, alky, aryl, alkene, alkyne, alkylaryl, and combinations thereof, wherein the linker does not abolish biologically activity, unless such abolition is at least partially relieved upon cleavage. Preferable, such cleavage is produced in a subject, more preferably in a target tissue in the subject.

Subjects contemplated by the invention include, but are not limited to, bacteria, cells, cell culture systems, plants, fungi, animals, such as an animal disease model, nematodes, insects, and/or mammals, such as humans.

The peptides of the invention may be formulated as a pharmaceutically acceptable compound or composition. Excipients, diluents and/or carriers are known in the art, for example, see REMINGTON'S PHARMACEUTICAL SCIENCES, 18th Ed. (1990, Mack Publishing Co., Easton, Pa.) and GOODMAN AND GILMAN'S, THE PHARMACOLOGICAL BASIS OF THERAPEUTICS ($10^{th}$ ed. 2001).

Apoptotic function, or apoptosis may be screened using any of the methods known in the art or described herein.

Materials and Methods

Cell lines and primary cells. The human cervical cancer cell line, HeLa, was maintained in Dulbecco's modified Eagle's medium (DMEM) (BioWhittaker, Walkersville, Md.) supplemented with 10% fetal calf serum (FCS), with or without 1% penicillin-streptomycin-L-glutamate (PSG) (Invitrogen, Carlsbad, Calif.). The human T-cell line SupT1 was propagated in RPMI 1640 (BioWhittaker, Walkersville, Md.) supplemented with 10% FCS. Primary human $CD4^+$ lymphocytes were first isolated in buffy coats using vacutainer cell preparation tubes according to the manufacturer's protocol (Becton Dickinson, Franklin Lakes, N.J.). Buffy coats were then purified further using a $CD4^+$ isolation kit (Dynal Biotechnology, Olso, Norway) according to the manufacturer's instructions. Isolated lymphocytes were cultured in RPMI 1640 supplemented with 100 u/ml IL-2 (National Institute of Health, AIDS research and reference reagent program, Rockville, Md.), 6 µg/ml Phytohemaglutinin (Sigma Aldrich, St. Louis, Mo.; L-9017), and 10% FCS, for a period of 4 days prior to transduction. Following transduction, primary lymphocytes were cultured in RPMI 1640 supplemented with 10% FCS and 100 u/ml IL-2. $Hus1^{-/-}p21^{-/-}$ and $Hus1^{+/+p}$ $21^{-/-}$ mouse embryonic fibroblasts were cultured on glycerin-coated plates with RPMI medium (Invitrogen) supplemented with 10% fetal bovine serum (FBS), 1% PSG, and 10 mM nonessential amino acids (Invitrogen). Primary human thymic cultures were prepared as previously described (44).

RNA interference. All siRNA treatments were performed with Dharmacon smart pool siRNA duplexes: GADD45 (Dharmacon, Lafeyette, Colo.; M-003893-00), ATR (Dharmacon, Lafeyette, Colo.; M-003202-01), ATM (Dharmacon, Lafeyette, Colo.; M-003201-01), CHK2 (Dharmacon, Lafeyette, Colo.; M-003256-03), and Scrambled siRNA (Dharmacon, Lafeyette, Colo.; D-001206-13-05). Smart pool siRNAs were transfected at a final concentration of 100 nm into exponentially growing HeLa cells with Lipofectamine 2000 or Oligofectamine (Invitrogen, Carlsbad, Calif.), all according to manufacturers' protocols.

Immunofluorescence staining. HeLa cells were harvested 48 h posttransduction by trypsinization. Single-cell suspensions of minced thymic tissue were prepared for immunostaining 20 h after HIV-1NL4-3 infection. Cells were fixed with 2% paraformaldehyde in phosphate-buffered saline (PBS) for 35 min at 4° C. and then washed three times for 5 min each time in PBS. All subsequent steps were carried out at room temperature. Samples were blocked and permeabilized for 20 min in blocking buffer (3% bovine serum albumin (BSA), 0.2% Triton X-100, and 0.01% skim milk in PBS). Primary antibody (rabbit anti-γ-H2AX (48) or rabbit anti-BRCA1 (Bethyl Laboratories, Montgomery, Tex.)) was diluted 1:400 in incubation buffer (1% BSA and 0.02% Triton X-100 in PBS) and incubated with cells for 45 min. Cells were washed with PBS, after which secondary antibody (goat anti-rabbit immunoglobulin G (IgG)-AlexaFluor568 conjugate (Molecular Probes, Eugene, Oreg.)) diluted 1:500 in incubation buffer was applied for 35 min. Cells were washed with PBS as before and mounted on glass slides by using Fluor Save reagent (CalBiochem, San Diego, Calif.). Cells were visualized for γ-H2AX or BRCA1 immunostaining and green fluorescent protein (GFP) expression by scanning fluorescence confocal microscopy (FluoView FV300; Olympus, Melville, N.Y.).

Cell cycle analysis. At 48 h after infection, cells were detached by trypsinization, washed with fluorescence-activated cell sorting (FACS) buffer (2% FBS and 0.02% sodium azide in PBS), fixed with 2% paraformaldehyde in PBS, and permeabilized with 0.01% Triton X-100 in PBS for 15 min. Cells were washed again with FACS buffer, incubated in DNA staining buffer (10 µg of propidium iodide/ml and 11.25 kU of RNase A/ml in FACS buffer) for 15 min, and analyzed by FACScan flow cytometry for GFP expression or DNA content (Beckton Dickinson, Franklin Lakes, N.J.). In experiments involving transduction with lentivirus vectors, experiments with 90% transduction efficiency or higher were analyzed. Cell cycle profiles were modeled by using ModFit software (Verity Software, Topsham, Me.).

Lentivirus vectors. Lentivirus vectors were produced by transient transfection of HEK293T cells. For defective lentivirus vector production, plasmids pHRGFP and pHR-Vpr were cotransfected with pCMVΔR8.2ΔVpr (4) and pHCMV-VSVG (3) by calcium phosphate-mediated transfection (53). Virus supernatants were collected at 48, 72, and 96 h post-transfection. Harvested supernatants were cleared by centrifugation at 2,000 rpm. Cleared supernatants were concentrated by ultracentrifagation at 25,000 rpm for 1.5 h at 4° C. Concentrated virus was allowed to resuspend overnight at 4° C., and the suspension was frozen at −80° C. for storage. Vector titers were measured by infection of HeLa cells as described herein, followed by flow cytometric analysis of cells that were positive for the reporter molecule, GFP. Vector titers were calculated with the equation $[(F \times C_0)/V] \times D$, where F is the frequency of GFP-positive cells found by flow cytometry, $C_0$ is the total number of target cells at the time of infection, V is the volume of inoculum, and D is the virus dilution factor. The virus dilution factor used for titrations was 10. The total number of target cells at the time of infection was $10^6$. Infections were performed at a multiplicity of infection (MOI) of 2 or 2.5 with 10 µg of Polybrene/ml for 3 h. Infections of siRNA treated cells were performed 48 h after siRNA transfection.

HIV-1 infection. HIV-1NL4-3 stocks were prepared as previously described (20), diluted in Iscove's medium supplemented with 2% FBS and used to infect primary thymocytes at an MOI of 1.0.

Drug treatment. Cells were incubated with 10 mM hydroxyurea (HU) for 2 h before immunostaining was done.

Transduction methods. All transductions were carried out using a multiplicity of infection of 2. SupT1 and primary CD4+ lymphocytes were transduced with virus diluted in cell culture media with 8 µg/ml polybrene. Transduction was performed as previously described (51). HeLa cells were transduced in 6 well plates with virus diluted into cell culture media with 10 µg/ml polybrene. After 6 hours, virus was replaced with fresh culture media. Transduction efficiencies were verified by flow cytometry for each experiment to ensure that efficiencies were similar between treatments.

Western blotting procedures. All western blots were performed using the BioRad Criterion gel system (BioRad, Hercules, Calif.). Antibodies used were GADD45 (Santa Cruz Biotechnology, Santa Cruz, Calif.; sc-797), Actin (Santa Cruz Biotechnologies, Santa Cruz, Calif.; sc-797), CHK2 (Santa Cruz Biotechnology, Santa Cruz, Calif.; sc-8813), ATM (Novus Biologicals, Littleton, Colo.; catalog #100-104H1), phospho-JNK-Tyr183 (Cell Signaling Technology, Beverly, Mass.; catalog #9255S), phospho-p38 kinase (Promega, Madison; 15823207), JNK (Cell Signaling Technology, Beverly, Mass.; 9252), ATR (obtained from Dr. Paul Nghiem, Harvard), anti-rabbit secondary-HRP (Santa Cruz Biotechnology, Santa Cruz, Calif.; sc-2030), anti-goat secondary-HRP (Santa Cruz Biotechnology, Santa Cruz, Calif.; sc-2033), PARP (Cell Signaling Technology, Beverly, Mass.), BRCA1 phospho ser1423 (Bethyl Laboratories, Montgomery, Tex.) Rabbit primary antibodies against Rad17 (Santa Cruz Biotechnology, Santa Cruz, Calif.), and were applied for 90 min at room temperature. Blots were washed three times in TPBS (0.1% Tween 20 in PBS) for 10 min each time at room temperature.

Secondary horseradish peroxidase-conjugated goat anti-rabbit IgG antibodies were applied for 45 min at room temperature. Blots were washed again three times in TPBS before protein detection with enhanced chemiluminescence reagent (Amersham). HAtagged Vpr protein was detected with anti-HA antibodies. SupT1 cells were treated with Anisomycin (Sigma Aldrich, St. Louis, Mo.) at a concentration of 25 µg/ml for 30 minutes, then lysed immediately. Changes in protein levels observed by Western blot were assessed by densitometry scanning.

Cells were detached at the time of cell cycle analysis and lysed in Laemmli sodium dodecyl sulfate (SDS) sample buffer (60 mM Tris-HCl, 10% glycerol, 2% SDS, 0.1% bromophenol blue, and 14.4 mM 2-mercaptoethanol in double-distilled H2O) at a concentration of $5 \times 10^5$ cells/100 µl of buffer. Lysates were boiled for 5 min prior to being loaded on SDS-10% polyacrylamide gels for electrophoretic separation. Proteins were transferred to polyvinylidene difluoride membranes by a semidry transfer method (Bio-Rad, Hercules, Calif.) and then blocked for 45 min at room temperature in blocking solution (5% skim milk and 0.1% Tween 20 in PBS).

Apoptosis assays. Cells were fixed in 2% paraformaldehyde (in PBS) for 15 minutes at room temperature. Fixed cells were then permeabilized in 0.1% Triton X-100 (in PBS) for 15 minutes at room temperature, then washed 2 times in PBS and incubated in 0.5 µg/ml 4',6-diamidino-2-phenylindole, dihydrochloride (DAPI) (Molecular Probes, Eugene, Oreg.) dissolved in PBS, for 45 minutes at 37° C. DAPI-treated cells were then analyzed by fluorescence microscopy. Random fields were chosen throughout the dish and apoptotic cells were marked by the presence of fragmented nuclei. Total apoptotic cells from 3 independent experiments were counted and divided by the total cell number to obtain a percentage of apoptotic cells for each treatment with standard deviations. A minimum of 1000 cells were counted per treatment/per experiment. PARP cleavage was assayed by Western blot as described above.

In vitro kinase assay. SupT1 cells were infected with pHR-VPR and as a VPR-minus control, pHR-GFP, then lysed at 48 hours post-transduction with supplied lysis buffer. JNK kinase activity was measured with the SAPK/JNK non-radioactive assay kit (Cell Signaling Technology, Beverly, Mass.), according to the manufacturer's protocol.

Example I

Figure 1:
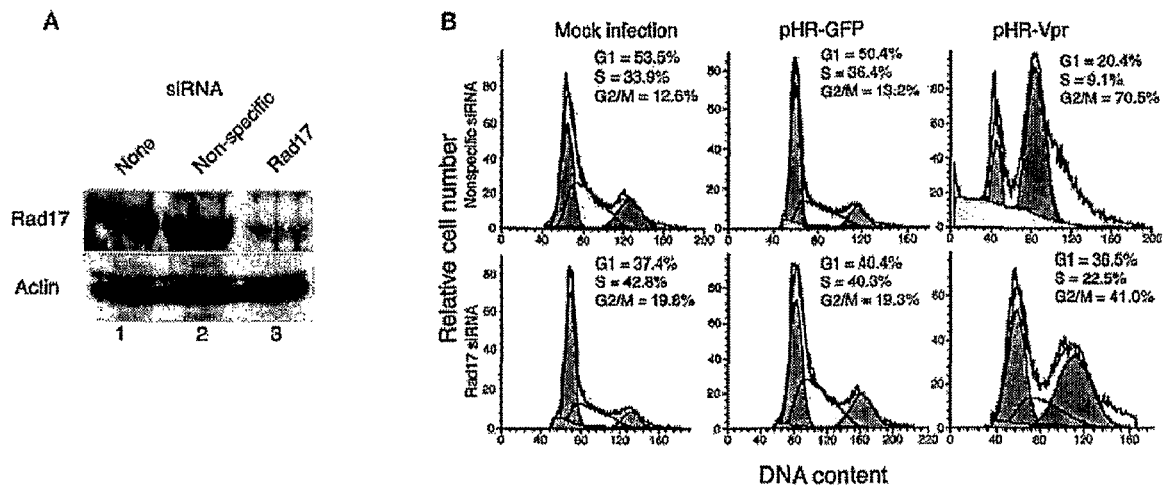
FIG. 1. Rad17 inhibition by RNA interference relieves Vpr-mediated G2 arrest.

Rad17 is necessary for Vpr-mediated $G_2$ arrest. To examine the role of Rad17 in Vpr-mediated $G_2$ arrest, RNA interference was used to reduce endogenous Rad17 levels. Transfected siRNA duplex oligonucleotides targeted at Rad17 mRNA (54) were used to knock down Rad17, in parallel, siRNA with a nonspecific target sequence and mock transfection was used as controls. In these experiments, endogenous Rad17 protein levels were reduced by approximately 85%, relative to those of mock-transfected or nonspecific siRNA-transfected cells (FIG. 1A). Following transfection, cells were transduced with lentivirus vectors expressing either Vpr and GFP cDNAs separated by an internal ribosome entry site (pHR-Vpr) or GFP alone (pHRGFP) (40) (79). At 48 h after transfection, cells were analyzed by flow cytometry for infection efficiency and DNA content, as reported by GFP expression and propidium iodide staining, respectively. Cell cycle distributions of the various experimental cell populations were analyzed after electronic gating of GFP-positive (transduced) and GFP-negative (untransduced) cells. Infection with pHR-GFP did not affect the cell cycle profile of any of the transfected populations. Infection with pHR-Vpr induced a marked accumulation of cells in $G_2$ phase (FIG. 1B). When cells were pretreated by transfection with a Rad17-specific siRNA (but not with nonspecific siRNA), Vpr-induced accumulation in $G_2$ was dramatically relieved (FIG. 1B). Therefore, Rad17 is required for activation of the $G_2$ checkpoint by Vpr.

Example II

Hus1 is necessary for Vpr-mediated $G_2$ arrest. Finding that Rad17 is necessary for Vpr-induced $G_2$ arrest, another constituent of the ATR signaling pathway, Hus1, was examined. To examine the role of Hus1 in Vpr-induced $G_2$ arrest, Hus1$^{-/-}$ p21$^{-/-}$ mouse embryonic fibroblasts (49) were used. Both Hus1$^{-/-}$ p21$^{-/-}$ cells and Hus1$^{+/+}$ p21$^{-/-}$ cells exhibited normal cell cycle distributions when mock infected or infected with pHR-GFP (FIG. 2). Hus1$^{-/-}$ p21$^{-/-}$ cells, however, failed to arrest in $G_2$ after infection with pHR-Vpr, whereas their Hus1$^{+/+}$ counterparts exhibited robust $G_2$ arrest (FIG. 2). These experiments illustrate a requirement for Hus1 in Vpr-induced $G_2$ arrest.

Taken together, the observations indicate that HIV-1 Vpr activates the $G_2$ checkpoint in a manner that is mechanistically similar to that of certain genotoxic agents (specifically, HU) that cause replication inhibition. Because recognition of DNA damage via ATR can lead to dramatic cellular changes, other than checkpoint activation, the consequences of ATR activation were examined. For example, the effect of Vpr on γ-H2AX was examined, as well as, BRCA1, because they have been reported to recruit DNA repair factors and induce apoptosis.

Example III

Figure 3:
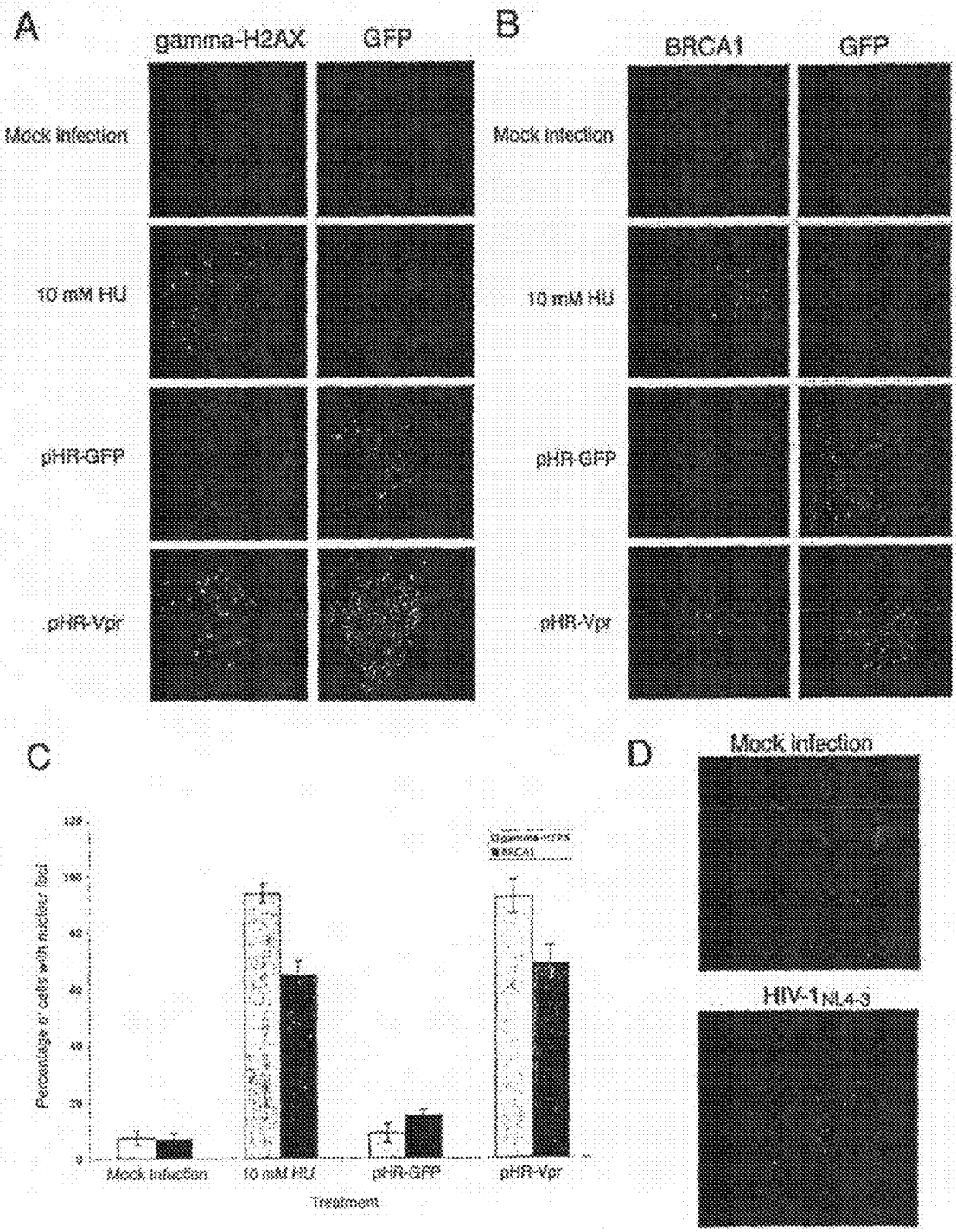
FIG. 3. Vpr induces γ-H2AX and BRCA1 focus formation.

Vpr expression induces γ-H2AX and BRCA1 focus formation. It was possible that Vpr, through ATR activation, would induce γ-H2AX (9) and BRCA1 (45) focus formation. To test this hypothesis, HeLa cells were infected with pHR-Vpr or pHR-GFP and, 48 h later, immunostained with γ-H2AX- or BRCA1-specific antibodies. As a positive control, nontransduced cells were treated for 1 h with 10 mM HU 10 min prior to immunostaining (46). Samples then were visualized by fluorescence scanning confocal microscopy (FIGS. 3A and B). Cells with multiple (10 or more), intense nuclear foci were manually counted. These quantitations are presented in FIG. 3C. Approximately 93 or 69% of Vpr-expressing cells exhibited significant γ-H2AX or BRCA1 focal staining, respectively, whereas only 9 or 16% of pHR-GFP infected cells exhibited any γ-H2AX or BRCA1 foci, respectively. Less than 8% of mock-infected cells exhibited γ-H2AX or BRCA1 foci. Approximately 94 or 65% of HU-treated cells exhibited γ-H2AX or BRCA1 foci, respectively. Therefore, it is concluded that Vpr expression leads to γ-H2AX and BRCA1 focus formation. However, the phosphorylation status of BRCA1 was not formally proven by the above experiments, because recognition by the BRCA1-specific antibody used in this experiment was not dependent on BRCA1 phosphorylation.

Figure 7:
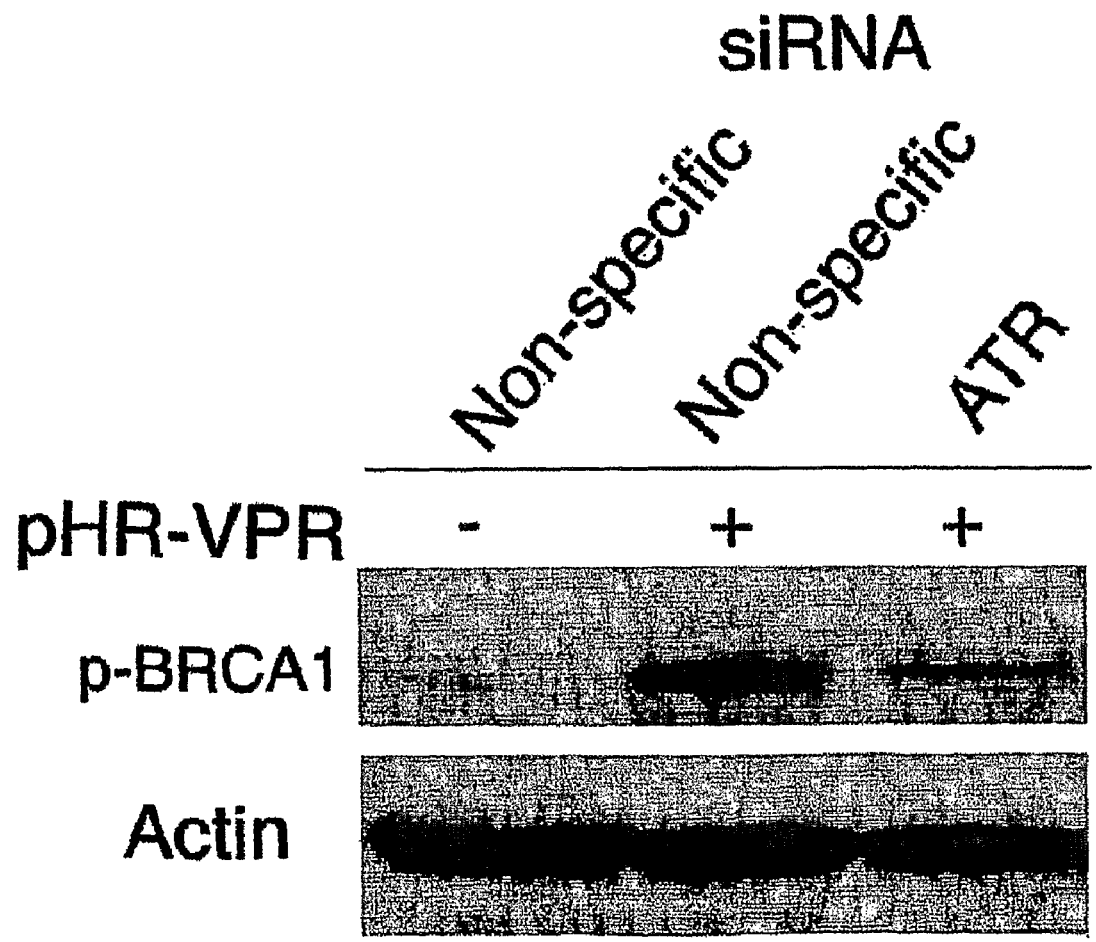
FIG. 7. Vpr induces ATR-dependent phosphorylation of BRCA1 at serine 1423. HeLa cells were either mock treated or transduced with pHR-VPR in the presence of either non-specific siRNA or siRNA targeted to ATR. Cell lysates were harvested 48 hours posttransduction then subject to Western blot analysis with anti-BRCA1 phospho-serine 1423 antibodies.
Figure 8:
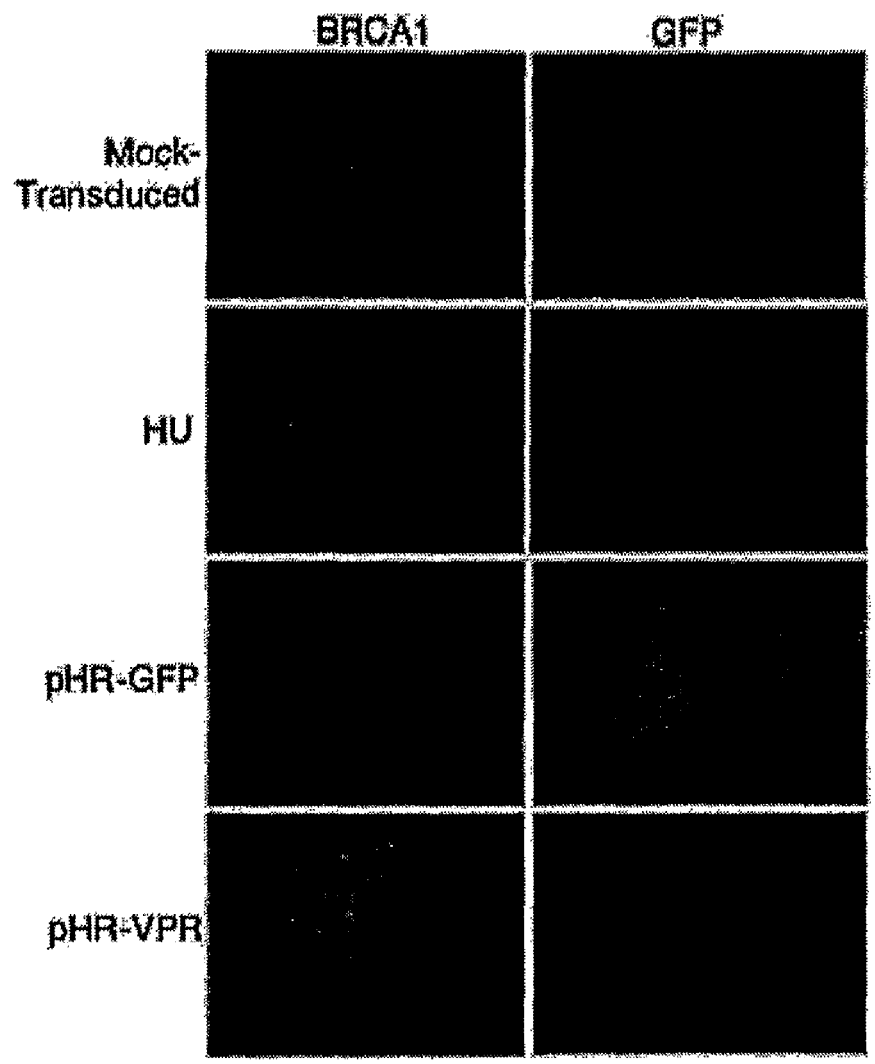
FIG. 8. Vpr activates BRCA1, as evidenced by BRCA1 nuclear foci formation. HeLa cells were transduced with either pHR-VPR, or pHR-GFP. As a positive control, HeLa cells were treated with HU. 2 hours post-HU treatment, and 48 hours post-transduction, cells were subject to an immunofluorescence assay with BRCA1-specific antibodies and analyzed by laser scanning confocal microscopy.

Phosphorylation of BRCA1 at serine 1423 by HIV-1 Vpr is ATR-dependent. Following DNA damage, ATR phosphorylates BRCA1 at serine 1423 (45, 63). To determine whether Vpr induced the phosphorylation of BRCA1 at serine 1423 in an ATR-dependent manner, HeLa cells were infected with pHR-VPR and examined for the phosphorylation of BRCA1 at serine 1423, in the presence of either non-specific or ATR-specific siRNA. Vpr induced phosphorylation of BRCA1 at serine 1423 (FIG. 7A). Treatment of HeLa cells with ATR-specific siRNA prior to transduction relieved Vpr-induced phosphorylation of BRCA1, which indicated the phosphorylation was ATR-dependent (FIG. 7A).

Example IV

HIV-1 infection induces γ-H2AX foci in primary CD4$^+$ thymocytes. The $G_2$ arrest effect of Vpr is identical in many human cell lines tested and in primary lymphocytes (21, 41, 53). Therefore, HeLa cells, although not a target for HIV-1, constitute model cells in which to study the mechanism of $G_2$ arrest by Vpr. Nonetheless, to confirm our observations in HeLa cells, primary human CD4$^+$ cells infected with full-length HIV-1 were tested. Primary human CD4$^+$ thymocytes were infected with full-length HIV-1$_{NL4-3}$ (2) or mock infected. At 20 h after infection, cells were immunostained for γ-H2AX (FIG. 3D). NL4-3 infection caused a staining pattern of distinct γ-H2AX nuclear foci that was not observed in mock-infected cells. These data indicate that full-length HIV-1 induces γ-H2AX focus formation in primary CD4$^+$ cells and confirm the applicability of HeLa cells.

Example V

ATR, but not ATM, is necessary for Vpr-induced $G_2$ arrest. ATR is primarily responsible for $G_2$ checkpoint activation via Chk1 phosphorylation (25). However, it has been shown that ATM, which acts primarily on Chk2, can play a minor, more transient role in Chk1 phosphorylation (1). Although Bartz and colleagues demonstrated that ATM$^{-/-}$ cells were able to arrest in $G_2$ in response to Vpr (8), a partial role for ATM would be formally possible. Specifically, two observations prompted reexamination of the role of ATM. First, suppression of ATR or Chk1 by RNA interference is typically unable to completely relieve Vpr-induced $G_2$ arrest (40). It is possible that residual ATR and/or Chk1 levels were responsible for the partial accumulation of cells in $G_2$. Alternatively, the low level of $G_2$ arrest in the context of ATR- and/or Chk1-specific inhibition could have been attributable to ATM. The second finding that prompted reexamination of the role of ATM was that caffeine, an inhibitor of both ATR and ATM, was able to completely relieve Vpr-induced $G_2$ arrest (40, 53).

Figure 4:
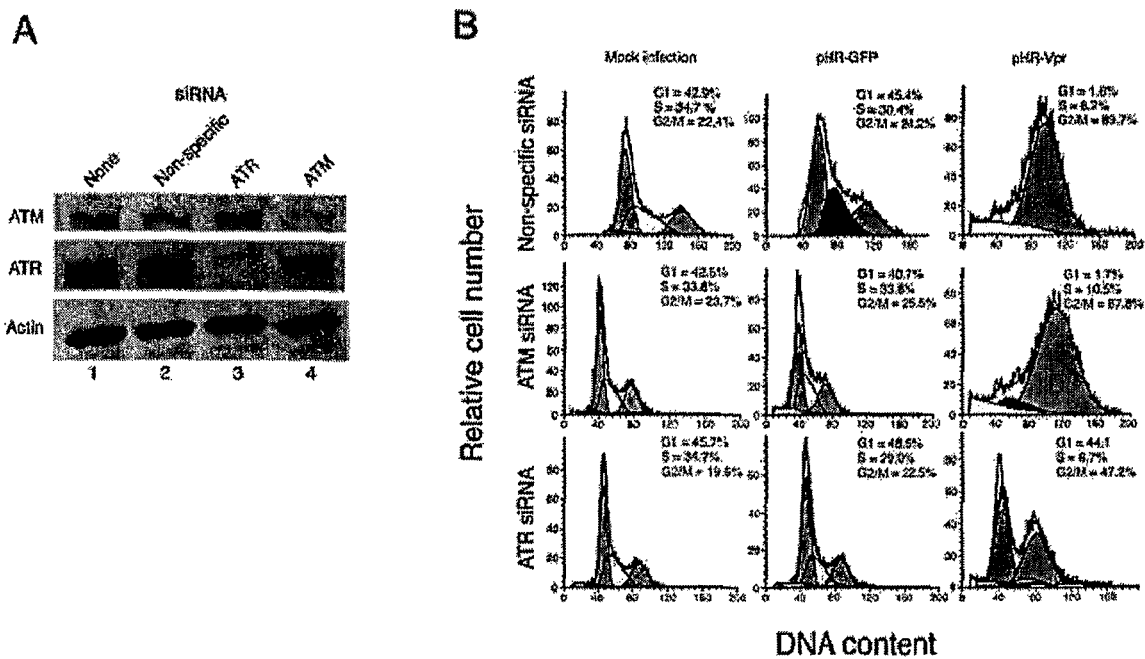
FIG. 4. ATM is not necessary for Vpr-mediated G2 arrest.

To test the potential contribution of ATM activity to Vpr-induced $G_2$ arrest, siRNA directed at ATR and ATM were transfected, in combination or separately, the cells were then infected with pHR-VPR or control vectors. As expected, pretreatment with ATR-specific siRNA produced a marked, although incomplete, alleviation of $G_2$ arrest by Vpr (FIG. 4). Pretreatment with ATM-specific siRNA, which reduced ATM protein levels by 85%, relative to those in mock-treated cells (FIG. 4A), produced no change in cell cycle arrest by Vpr compared with the results seen in cells transfected with non-specific siRNA or no siRNA (FIG. 4B). In addition, simultaneous suppression of ATR and ATM did not produce any additional relief of $G_2$ arrest (data not shown). Therefore, these results indicate that ATM is dispensable for Vpr-induced $G_2$ checkpoint activation (8).

Example VI

Figure 6A:
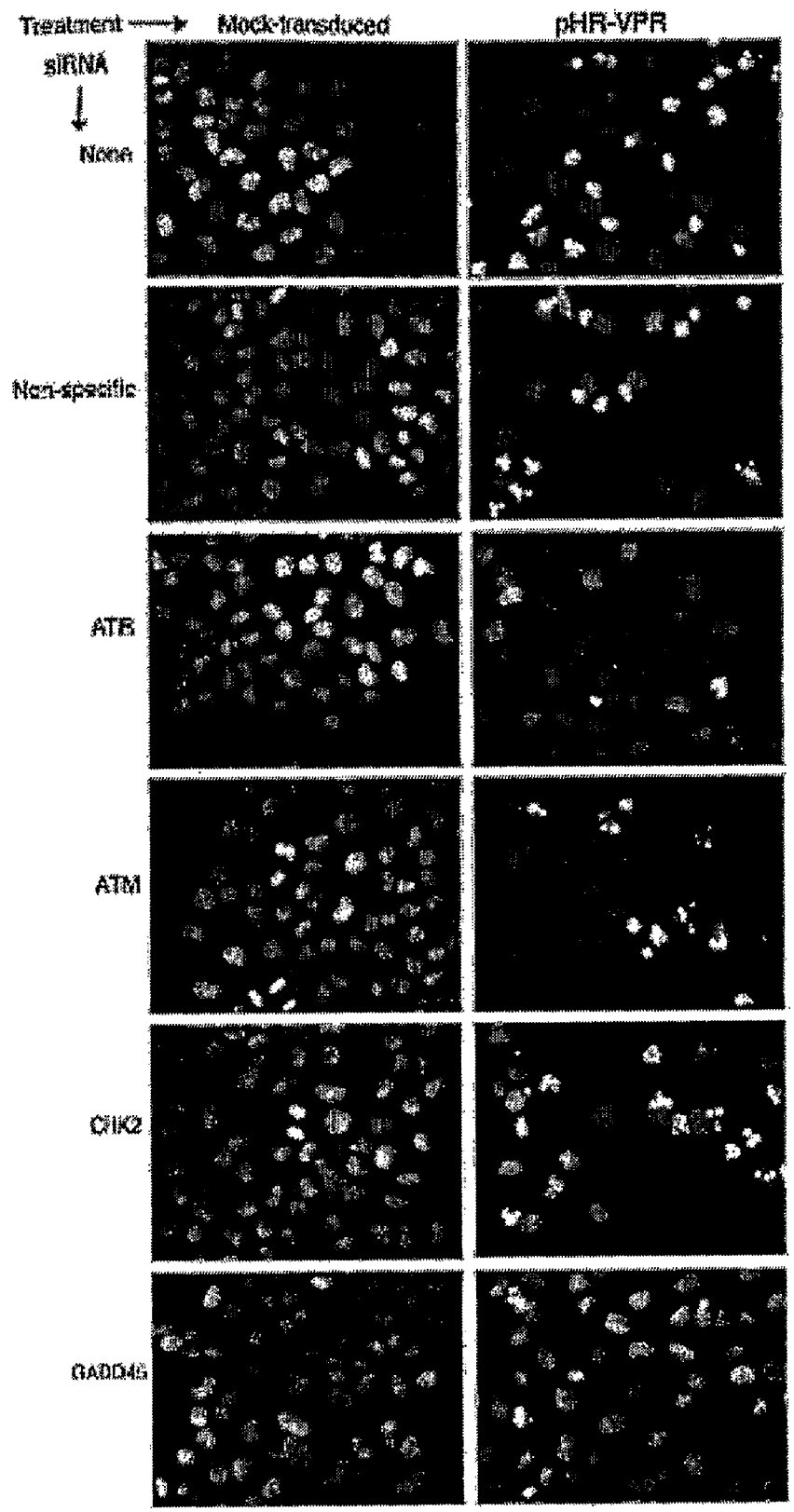
FIG. 6A shows HeLa cells that were transfected with non-specific (NS) siRNA or siRNA targeted to ATM, CHK2, ATR or GADD45 then, 48 hours post-transfection, cells were mock-transduced or transduced with pHR-VPR.
Figure 6B:
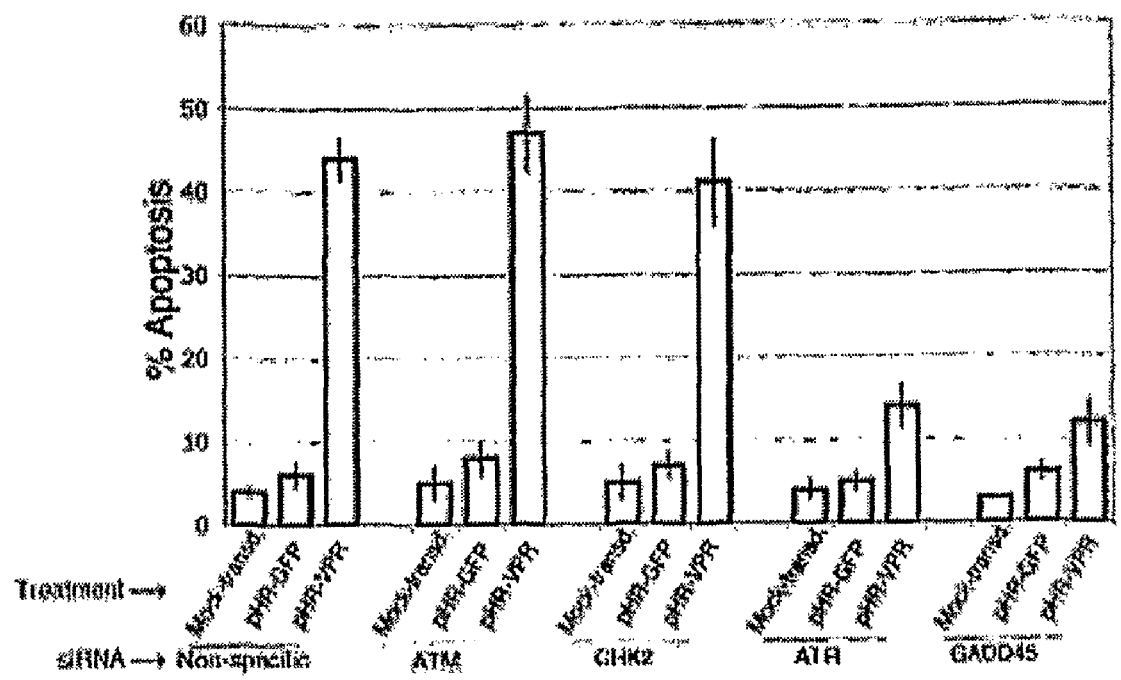
FIG. 6B illustrates the results from 3 independent experiments described in panel A that were quantitated.
Figure 6C:
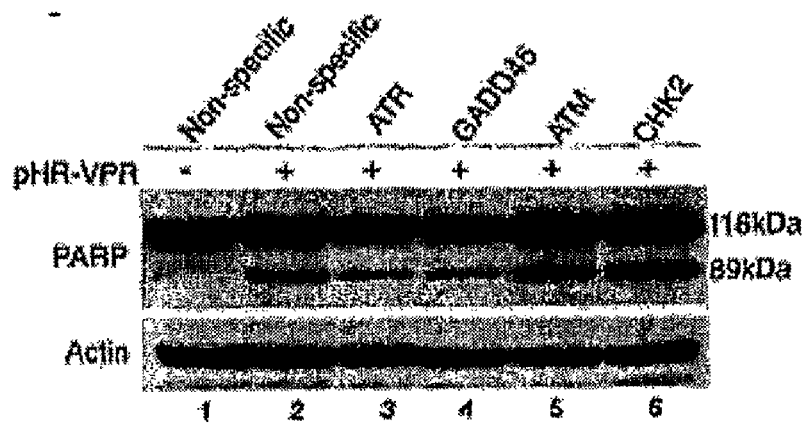
FIG. 6C shows Western analysis of Hela cells that were either mock treated or transduced with pHR-VPR in the presence of non-specific siRNA or siRNA targeted to ATR, GADD45, ATM, or CHK2. 48 hours post-transduction, cell lysates were harvested and subject to Western blot analysis with anti-PARP antibodies that recognize both full length PARP and caspase cleaved (89 kDa) PARP.
Figure 6D:
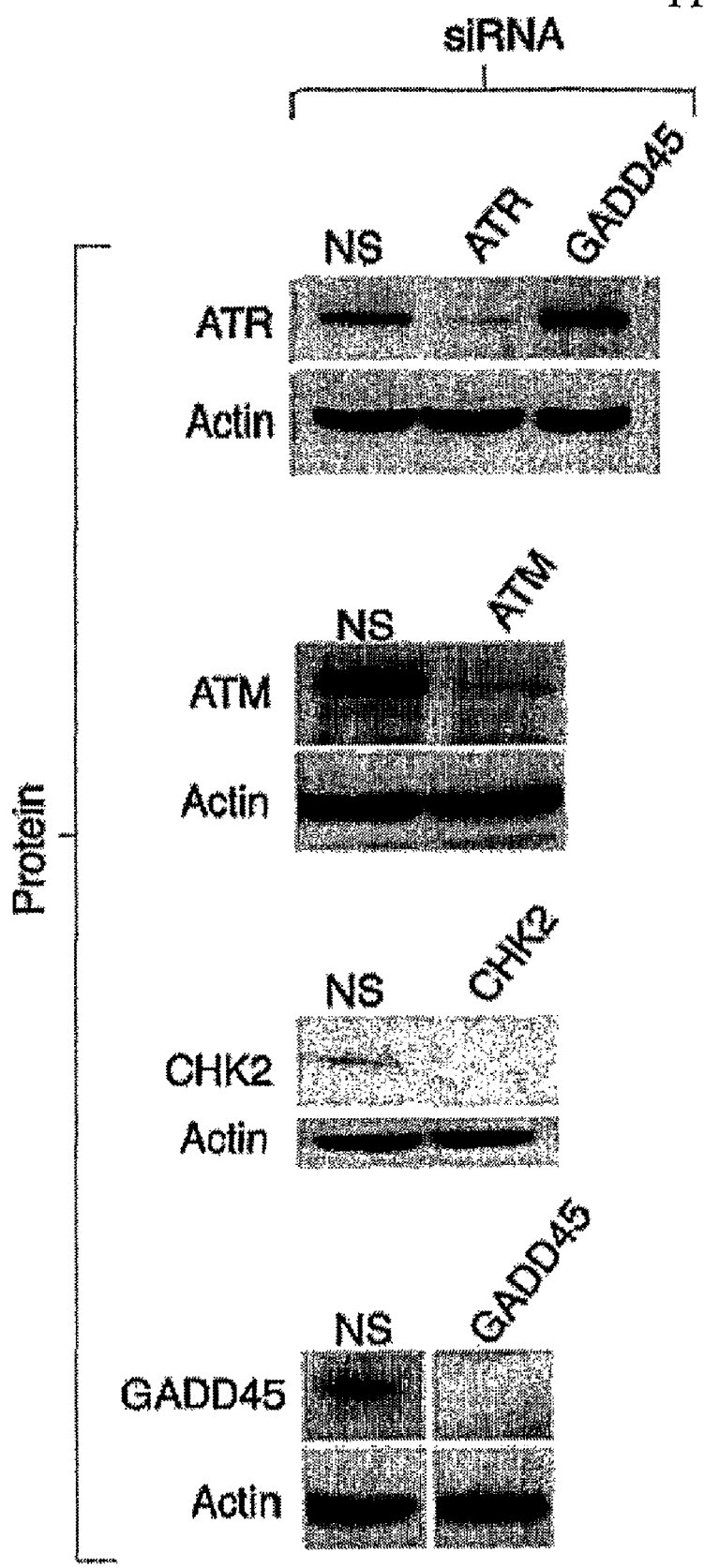
FIG. 6D shows cells that were treated with indicated siRNAs, lysed, and each siRNA treatment was assayed by Western blot to verify knockdown.
Figure 6E:
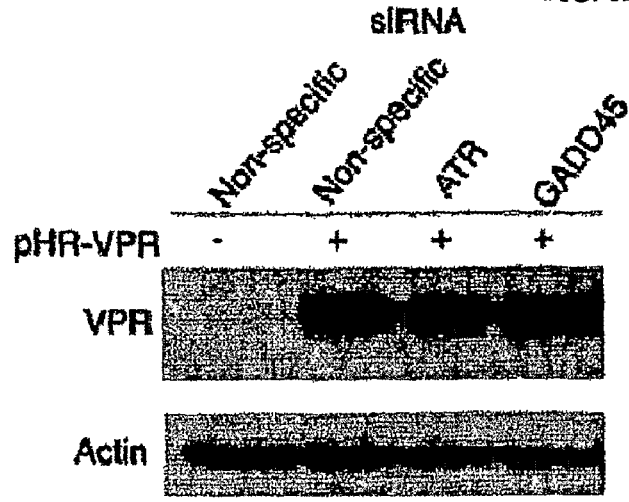
FIG. 6E illustrates that the siRNA treatments did not affect pHR-VPR expression, by showing lysates from each siRNA treatment that were assayed by western blot for Vpr protein levels.

ATR is required for apoptosis induced by HIV-1 Vpr. Vpr-induced $G_2$ arrest is signaled via the ATR DNA damage pathway. To investigate ATR in the context of Vpr-induced apoptosis, HeLa cells were transfected with short-interfering RNA (siRNA) duplexes directed at ATR or non-specific siRNA and then cells were transduced with lentiviral vectors expressing either HIV-1NL4-3 Vpr and GFP (pHR-VPR), or GFP alone (pHR-GFP). The construct, pHR-VPR, expresses Vpr and GFP from a dicistronic mRNA that uses an intervening internal ribosome entry site (IRES) (77, 79). To examine Vpr-induced apoptosis, cells were treated with the nuclear stain, 4'6-diamidino-2-phenylindole dihydrochloride (DAPI), and the nuclear morphology (FIG. 6A) was examined. Treatment of pHR-VPR-transduced cells with ATR-specific siRNA resulted in a 67% decrease in apoptosis (FIG. 6B). This reduction in apoptosis correlated with a reduction in G2 arrest. As a control, siRNAs against ATM or CHK2 were used. ATM is a close relative of ATR that is dispensable for Vpr-induced G2 arrest (see, Example V). CHK2 is a checkpoint kinase that is activated by ATM. Knockdown of ATM or CHK2 produced no appreciable changes in the level of apoptosis induced by Vpr (FIG. 6B). None of the siRNA treatments had a significant effect on apoptosis in mock-treated or pHR-GFP-transduced cells (FIG. 1b). In addition to measuring apoptosis by DAPI staining, the results were confirmed by measuring caspase-induced cleavage of poly(ADP-ribose) polymerase (PARP). PARP cleavage produces an 89 kDa fragment that is an early result of caspase activation which precedes DNA cleavage (84, 85), and is essential for progression into apoptosis (reviewed in (56)). ATR knockdown resulted in a marked decrease in PARP cleavage compared to nonspecific, ATM, and CHK2 siRNA treatments (FIG. 6C, compare lanes 2, 3, 5, 6). Kockdown of the corresponding proteins by each of the siRNAs was evaluated by Western blot (FIG. 6D). To rule out the possibility that ATR- or GADD45-specific siRNA treatments may relieve the effects of Vpr by disrupting expression of Vpr itself rather than affecting the function of ATR or GADD45, Vpr protein levels were analyzed by Western blot analysis (FIG. 6E). None of the siRNA treatments had any appreciable effect on Vpr protein levels.

Example VII

Knockdown of GADD45 relieves Vpr-induced apoptosis. Recent reports have suggested that GADD45 is a transcriptional target of BRCA1 (65, 71, 72), involved in the induction of apoptosis (65). Based on these reports, and the present observation that BRCA1 is activated in response to Vpr, GADD45 was examined for a role in Vpr-induced apoptosis. To examine whether GADD45 is required for Vpr-induced apoptosis, HeLa cells were treated with non-specific siRNA and GADD45-specific siRNA, transduced with vpr- or gfp-expressing viruses, and apoptosis measured by DAPI staining (FIG. 6A). Efficient knockdown of GADD45 resulted in a 70% decrease in Vpr-induced apoptosis (FIG. 6B). ATM, CHK2, and non-specific siRNA treatments had any appreciable effect on Vpr-induced apoptosis (FIG. 6B). PARP cleavage was then assayed to verify the results from our DAPI experiments. As observed with ATR knockdown, GADD45 knockdown prior to pHR-VPR transduction resulted in a marked reduction in PARP cleavage (FIG. 6C, compare lanes 2, 4-6).

Example VIII

Figure 9A:
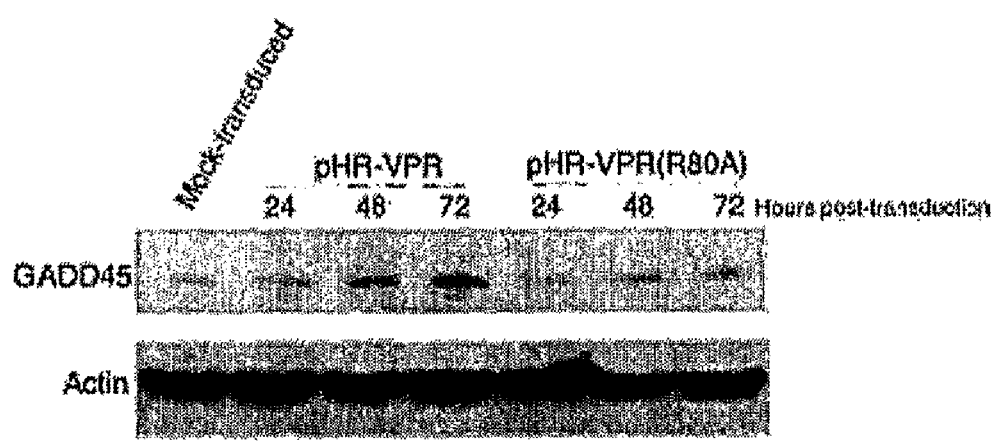
FIG. 9. Vpr upregulates GADD45 protein levels in both SupT1 cells, and primary human CD4+ lymphocytes. (a) SupT1 cells were transduced with pHR-VPR or pHR-GFP, then harvested 24, 48, and 72 hours post-transduction. Cell lysates from each timepoint were subject to Western blot analysis with polyclonal antibodies against GADD45. (b) Primary human CD4+ lymphocytes were transduced with pHR-VPR or pHR-VPR(R80A), then harvested 48 and 72 hours post-transduction. Primary cell lysates were subject to Western blot analysis with polyclonal antibodies against GADD45. Transduction efficiencies for both pHR-VPR and pHR-VPR(R80A) in primary CD4+ lymphocytes were between 25% to 30%, a marked reduction from efficiencies observed in SupT1 cells which ranged from 70% to 80%.
Figure 9B:
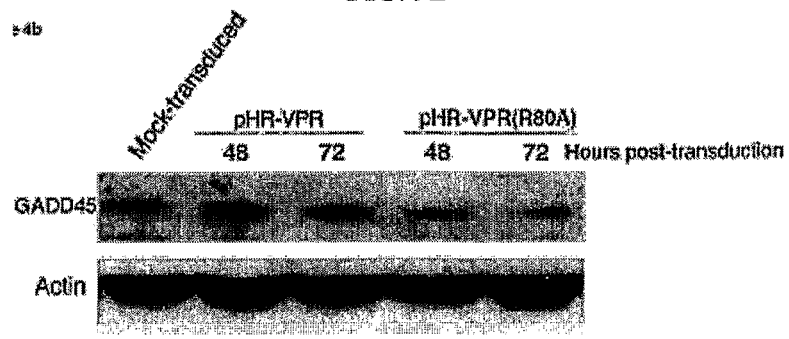

HIV-1 Vpr upregulates GADD45 protein levels in primary CD4+ lymphocytes and SupT1 cells. Based on the observation that GADD45 was required for Vpr-induced apoptosis, it was hypothesized that vpr expression would lead to upregulation of GADD45. To determine whether Vpr expression resulted in upregulation of GADD45 protein, SupT1 cells (a CD4+ lymphocyte cell line) and HeLa cells (HeLa cell data not shown) were transduced with pHR viruses. Cells were lysed at 24, 48 and 72 hours post-transduction and GADD45 protein levels were measured by Western blot analysis. A 3-fold upregulation of GADD45 protein was detected at 48 hours post-transduction in pHR-VPR-transduced cell lysates, in comparison to lysates from cells transduced with pHR-GFP (FIG. 9A). These results prompted the examination of Vpr-induce upregulation of GADD45 in primary human CD4+ lymphocytes, a physiologically relevant target of HIV-1. As an additional negative control, a viral vector that expressed vpr with the mutation R80A (64) was used. A previous report established that Vpr(R80A) is unable to induce $G_2$ arrest and apoptosis (64). Therefore, if an increase in GADD45 expression was the principal mediator of Vpr-induced apoptosis, then Vpr(R80A) should not be capable of such an increase. Similar to our results in cell lines, transduction of primary human CD4+ lymphocytes with pHR-VPR resulted in a 4-fold upregulation of GADD45 protein (FIG. 9B). In comparison, transduction with pHRVPR(R80A) did not induce GADD45 upregulation above levels observed in mock-transduced lysates (FIG. 9B).

Example IX

Figure 10:
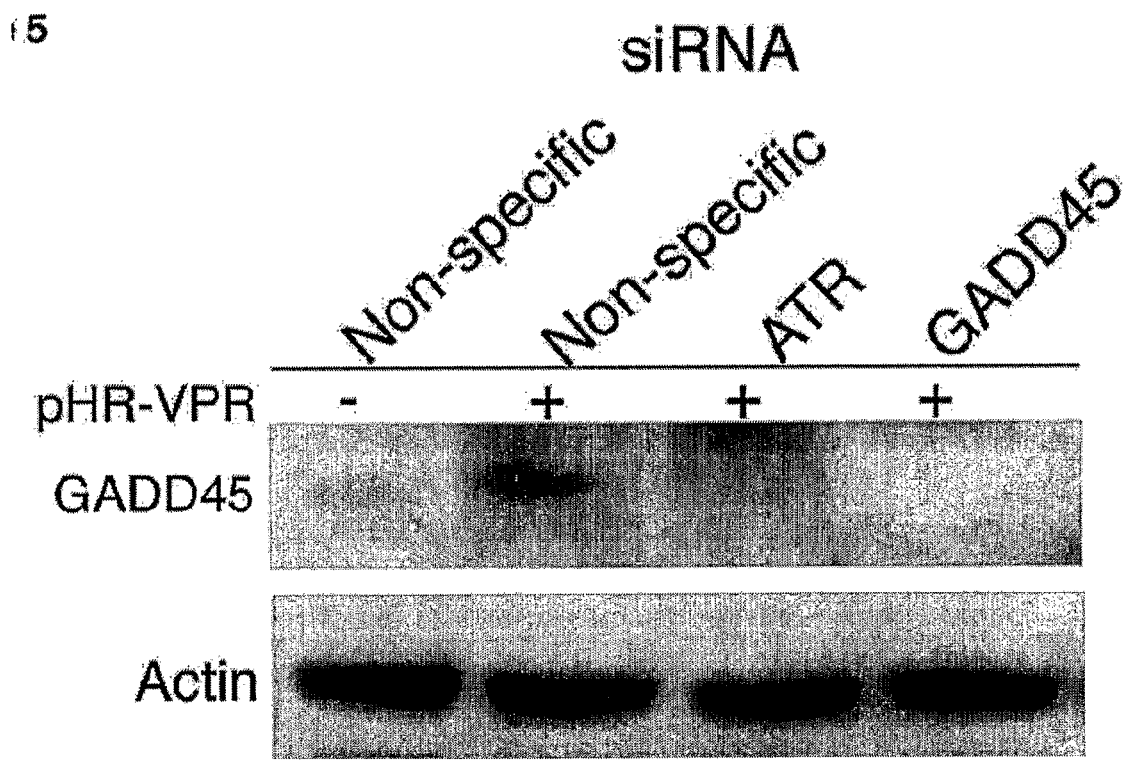
FIG. 10. Vpr-induced upregulation of GADD45 is ATR-dependent. HeLa cells were transfected with either non-specific siRNA, GADD45-specific siRNA, or ATR-specific siRNA, then mock-transduced or transduced with pHR-VPR. The cells were lysed at 48 hours posttransduction and subject to Western blot with polyclonal antibodies against GADD45.

Induction of GADD45 by Vpr is ATR-dependent. Although overexpression of BRCA1, a known target of ATR, has been shown to transcriptionally upregulate GADD45 (65), no functional relationship has previously been established between ATR and GADD45. To determine whether GADD45 induction by Vpr was dependent on signaling via ATR, a knockdown of ATR was used to assay impairment of upregulation of GADD45. HeLa cells were transfected with ATR siRNA or scrambled siRNA, and then transduced with pHR viruses, as previously described. At 48 hours post-transduction, GADD45 protein levels were measured by Western blot (FIG. 10). Knockdown of ATR resulted in abrogation of Vpr-induced GADD45 upregulation. As a control experiment, knockdown of GADD45 with siRNA did not reduce ATR protein levels (FIG. 6D). This confirms that Vpr upregulates GADD45 via ATR.

Example X

Figure 11A:
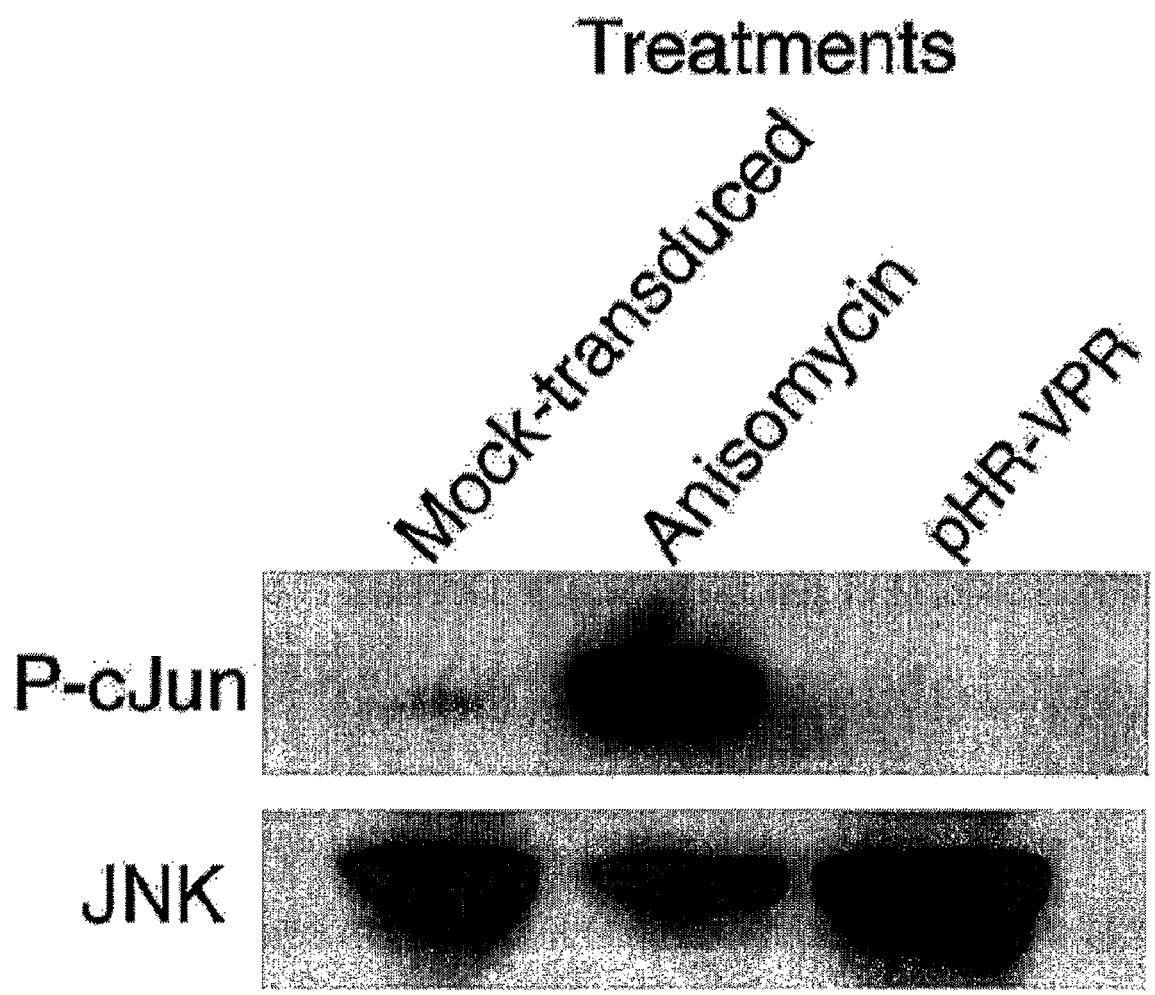
FIG. 11. Vpr-induced upregulation of GADD45 does not result in activation of JNK or p38 kinase. (a) SupT1 cells were transduced with pHR-VPR. At 48 hours post-transduction, cells were lysed and incubated with recombinant c-Jun. The relative levels of c-Jun phosphorylation for each treatment were determined by western blot, using phospho-specific antibodies against c-Jun. As a positive control, cells were treated with Anisomycin to induce JNK activation. (b) SupT1 cells were transduced with pHR-VPR then lysed at 24, 48, and 72 hours posttransduction. VPR-induced phosphorylation of p38 kinase was determined by western blot using a phospho-specific antibody against p38 kinase. As a positive control, cells were treated with Anisomycin to induce p38 kinase activation.

Induction of apoptosis by Vpr is not mediated by activation of the MAP kinases, JNK or p38. Considering earlier reports that GADD45 activates a mitogen-activated protein kinase (MAPK) cascade culminating in Jun N-terminal kinase (JNK) activation and apoptosis (65), Vpr-induced apoptosis was examined for association with activation of JNK. Phosphorylation of c-Jun, a target of JNK, was measured in response to Vpr. As a positive control for JNK activation, cells were treated with anisomycin. Transduction of SupT1 cells with pHR-VPR did not result in any detectable phosphorylation of c-Jun (FIG. 11A). It remained possible that Vpr was activating JNK in a manner that does not result in phosphorylation of c-Jun, therefore, to measure JNK activation in a more direct manner, SupT1 cells were transduced with pHR-VPR, harvested and lysed at 24, 48 and 72 hours post-transduction. Cell lysates from each time point were subjected to Western blot with phosphor-specific antibodies against JNK. In agreement with the previous data, it was determined that JNK was not activated in response to Vpr (data not shown).

Figure 11B:
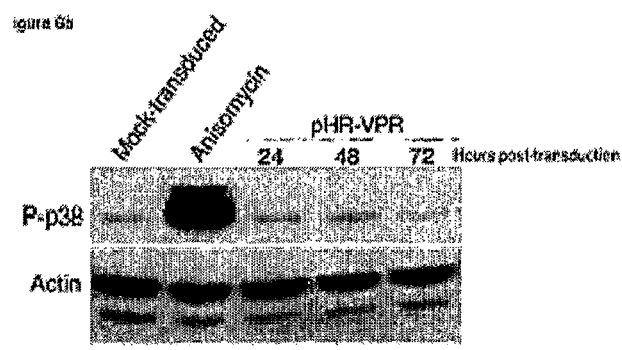

In view of the negative results concerning the role of JNK downstream from GADD45, p38 kinase, another member of the MAPK family implicated in apoptosis (77), was examined. SupT1 cells were transduced with pHR-VPR and harvested at 24, 48 and 72 hours post-infection, then assayed for the presence of activated, phosphorylated p38 kinase by Western blot. It was found that, like JNK, p38 kinase was not activated as result of Vpr-induced upregulation of GADD45 (FIG. 11B).

Example XI

Functional fragments of a protein, for example, Vpr, ATR, RAD17, BRAC1 and/or GADD45 retain the desired function. For example, a functional fragment of Vpr, wherein the function of interest is cell cycle arrest, is a fragment that retains the ability to produce a $G_2$ cell cycle arrest. A $G_2$ cell cycle arrest fragment of Vpr is identified by introducing one or more amino acid changes, or deletions into Vpr and assaying for $G_2$ arrest, for example, by FACs analysis.

Example XII

A compound may be screened for cell cycle arrest and/or apoptotic activity, for example, by administering a compound to a subject having an ATR protein and a BRAC1 protein, such as HeLa cells, SupT1 cells, primary cells and/or a mouse or rat, assaying for ATR dependent phosphorylation of BRAC1, and identifying a compound that either induces or inhibits $G_2$ cell cycle arrest and/or apoptosis.

SupT1 cells are cultured in a 96-well plate, a test compound is introduced into the desired wells, and cultured with the cells for an appropriate period of time. The cells are then transduced with pHR-VPR and assayed at 24, 48 and 72 hours post-infection for induction of apoptosis and/or $G_2$ cell cycle arrest. Compounds inhibiting apoptosis and/or $G_2$ cell cycle arrest are identified.

HeLa cells are cultured in a 96-well plate, a test compound is introduced into the desired wells, and cultured with the cells for an appropriate period of time. Control cells are transduced with pHR-VPR in the absence of a test compound. The cells may be harvested and assayed at 24, 48 and 72 hours post-infection for phosphorylation of BRAC1 or induction of apoptosis. Compounds capable of inducing apoptosis are identified as inducing a sufficient level of BRAC1 phosphorylation or inducing apoptosis, as compared to the control cells. Phosphorylation of BRAC1 is assayed for phosphorylation at serine 1423 using a phosphorylation specific antibody.

Example XIII

Functional fragments of a protein, for example, Vpr, ATR, RAD17, BRAC1 and/or GADD45 retain the desired function. For example, a functional fragment of Vpr, wherein the function of interest is inducing apoptosis similar to the mechanism induced by genotoxic agents. An apoptosis inducing fragment of Vpr is identified by introducing one or more amino acid changes, or deletions into Vpr and assaying for induction of apoptosis, for example, by treating cells exposed to the Vpr fragment with a nuclear stain, such as 4'6-diamidino-2-phenylindole dihydrochloride (DAPI), and examining the nuclear morphology of the cells.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

All references, including publications, patents, and patent applications, cited herein are hereby incorporated by reference to the same extent as if each reference were individually and specifically indicated to be incorporated by reference and were set forth in its entirety herein.

REFERENCES

1. Abraham, R. T. 2001. Cell cycle checkpoint signaling through the ATM and ATR kinases. Genes Dev. 15:2177-2196.
2. Adachi, A., H. E. Gendelman, S. Koenig, T. Folks, W. R., A. Rabson, and M. A. Martin. 1986. Production of acquired immunodeficiency syndromeassociated retrovirus in human and nonhuman cells transfected with an infectious molecular clone. J. Virol. 59:284-291.
3. Akkina, R. K., R. M. Walton, M. L. Chen, Q. X. Li, V. Planelles, and I. S. Chen. 1996. High-efficiency gene transfer into CD34[+] cells with a human immunodeficiency virus type 1-based retroviral vector pseudotyped with vesicular stomatitis virus envelope glycoprotein G. J. Virol. 70:2581-2585.
4. An, D. S., K. Morizono, Q. X. Li, S. H. Mao, S. Lu, and I. S. Chen. 1999. An inducible human immunodeficiency virus type 1 (HIV-1) vector which effectively suppresses HIV-1 replication. J. Virol. 73:7671-7677.
5. An, D. S., Y. Xie, S. H. Mao, K. Morizono, S. K. Kung, and I. S. Chen. 2003. Efficient lentiviral vectors for short hairpin RNA delivery into human cells. Hum. Gene Ther. 14:1207-1212.
6. Anderson, J., A. Banerjea, V. Planelles, and R. Akkina. 2003. Potent suppression of HIV type 1 infection by a short hairpin anti-CXCR4 siRNA. AIDS Res. Hum. Retrovir. 19:699-706.
7. Anderson, L., C. Henderson, and Y. Adachi. 2001. Phosphorylation and rapid relocalization of 53BP1 to nuclear foci upon DNA damage. Mol. Cell. Biol. 21:1719-1729.
8. Bartz, S. R., M. E. Rogel, and M. Emerman. 1996. Human immunodeficiency virus type 1 cell cycle control: Vpr is cytostatic and mediates $G_2$ accumulation by a mechanism which differs from DNA damage checkpoint control. J. Virol. 70:2324-2331.
9. Brown, E. J., and D. Baltimore. 2003. Essential and dispensable roles of ATR in cell cycle arrest and genome maintenance. Genes Dev. 17:615-628.
10. Burma, S., B. P. Chen, M. Murphy, A. Kurimasa, and D. J. Chen. 2001. ATM phosphorylates histone H2AX in response to DNA double-strand breaks. J. Biol. Chem. 276:42462-42467.
11. Cam, H., and B. D. Dynlacht. 2003. Emerging roles for E2F: beyond the G1/S transition and DNA replication. Cancer Cells 3:311-316.
12. Chowdhury, I. H., X. F. Wang, N. R. Landau, M. L. Robb, V. R. Polonis, D. L. Birx, and J. H. Kim. 2003. HIV-1 Vpr activates cell cycle inhibitor p21/Waf1/Cip1: a potential mechanism of $G_2$/M cell cycle arrest. Virology 305:371-377.

13. Deming, P. B., K. G. Flores, C. S. Downes, R. S. Paules, and W. K. Kaufmann. 2002. ATR enforces the topoisomerase II-dependent $G_2$ checkpoint through inhibition of Plk1 kinase. J. Biol. Chem. 277:36832-36838.

14. Emerman, M., and M. H. Malim. 1998. HIV-1 regulatory/accessory genes: keys to unraveling viral and host cell biology. Science 280:1880-1884.

15. Furuta, T., H. Takemura, Z. Y. Liao, G. J. Aune, C. Redon, O. A. Sedelnikova, D. R. Pilch, E. P. Rogakou, A. Celeste, H. T. Chen, A. Nussenzweig, M. I. Aladjem, W. M. Bonner, and Y. Pommier. 2003. Phosphorylation of histone H2AX and activation of Mre11, Rad50, and Nbs1 in response to replication-dependent DNA double-strand breaks induced by mammalian DNA topoisomerase I cleavage complexes. J. Biol. Chem. 278:20303-20312.

16. Geleziunas, R., W. Xu, K. Takeda, H. Ichijo, and W. C. Greene. 2001. HIV-1 Nef inhibits ASK1-dependent death signalling providing a potential mechanism for protecting the infected host cell. Nature 410:834-838.

17. Goh, W. C., N. Manel, and M. Emerman. 2004. The human immunodeficiency virus Vpr protein binds Cdc25C: implications for $G_2$ arrest. Virology 318:337-349.

18. He, J., S. Choe, R. Walker, P. Di Marzio, D. O. Morgan, and N. R. Landau. 1995. Human immunodeficiency virus type 1 viral protein R (Vpr) arrests cells in the $G_2$ phase of the cell cycle by inhibiting p34cdc2 activity. J. Virol. 69:6705-6711.

19. Hsieh, J. K., D. Yap, D. J. O'Connor, V. Fogal, L. Fallis, F. Chan, S. Zhong, and X. Lu. 2002. Novel function of the cyclin A binding site of E2F in regulating p53-induced apoptosis in response to DNA damage. Mol. Cell. Biol. 22:78-93.

20. Jamieson, B. D., G. M. Aldrovandi, V. Planelles, J. B. Jowett, L. Gao, L. M. Bloch, I. S. Chen, and J. A. Zack. 1994. Requirement of human immunodeficiency virus type 1 nef for in vivo replication and pathogenicity. J. Virol. 68:3478-3485.

21. Jowett, J. B., V. Planelles, B. Poon, N. P. Shah, M. L. Chen, and I. S. Chen. 1995. The human immunodeficiency virus type 1 vpr gene arrests infected T cells in the $G_2$☐M phase of the cell cycle. J. Virol. 69:6304-6313.

22. Kitchen, S. G., and J. A. Zack. 1997. CXCR4 expression during lymphopoiesis: implications for human immunodeficiency virus type 1 infection of the thymus. J. Virol. 71:6928-6934.

23. Koka, P. S., D. G. Brooks, A. Razai, C. M. Kitchen, and J. A. Zack. 2003. HIV type 1 infection alters cytokine mRNA expression in thymus. AIDS Res. Hum. Retrovir. 19:1-12.

24. Levine, A. J. 1997. p53, the cellular gatekeeper for growth and division. Cell 88:323-331.

25. Liu, Q., S. Guntuku, X. S. Cui, S. Matsuoka, D. Cortez, K. Tamai, G. Luo, S. Carattini-Rivera, F. DeMayo, A. Bradley, L. A. Donehower, and S. J. Elledge. 2000. Chk1 is an essential kinase that is regulated by Atr and required for the G(2)/M DNA damage checkpoint. Genes Dev. 14:1448-1459.

26. Liu, X., and R. L. Erikson. 2002. Activation of Cdc2/cyclin B and inhibition of centrosome amplification in cells depleted of Plk1 by siRNA. Proc. Natl. Acad. Sci. USA 99:8672-8676.

27. Lou, Z., and J. Chen. 2003. BRCA proteins and DNA damage checkpoints. Front. Biosci. 8:s718-s721.

28. Lu, Y. L., P. Spearman, and L. Ratner. 1993. Human immunodeficiency virus type 1 viral protein R localization in infected cells and virions. J. Virol. 67:6542-6550.

29. Lum, J. J., O. J. Cohen, Z. Nie, J. G. Weaver, T. S. Gomez, X. J. Yao, D. Lynch, A. A. Pilon, N. Hawley, J. E. Kim, Z. Chen, M. Montpetit, J. Sanchez-Dardon, E. A. Cohen, and A. D. Badley. 2003. Vpr R77Q is associated with long-term nonprogressive HIV infection and impaired induction of apoptosis. J. Clin. Investig. 111:1547-1554.

30. Maser, R. S., O. K. Mirzoeva, J. Wells, H. Olivares, B. R. Williams, R. A. Zinkel, P. J. Farnham, and J. H. Petrini. 2001. Mre11 complex and DNA replication: linkage to E2F and sites of DNA synthesis. Mol. Cell. Biol. 21:6006-6016.

31. Nakamura, Y. 2004. Isolation of p53-target genes and their functional analysis. Cancer Sci. 95:7-11.

32. Nghiem, P., P. K. Park, Y. Kim Ys, B. N. Desai, and S. L. Schreiber. 2002. ATR is not required for p53 activation but synergizes with p53 in the replication checkpoint. J. Biol. Chem. 15:15.

33. Nyberg, K. A., R. J. Michelson, C. W. Putnam, and T. A. Weinert. 2002. Toward maintaining the genome: DNA damage and replication checkpoints. Annu. Rev. Genet. 36:617-656.

34. Pilch, D. R., O. A. Sedelnikova, C. Redon, A. Celeste, A. Nussenzweig, and W. M. Bonner. 2003. Characteristics of gamma-H2AX foci at DNA doublestrand break sites. Biochem. Cell Biol. 81:123-129.

35. Re, F., D. Braaten, E. K. Franke, and J. Luban. 1995. Human immunodeficiency virus type 1 Vpr arrests the cell cycle in $G_2$ by inhibiting the activation of p34cdc2-cyclin B. J. Virol. 69:6859-6864.

36. Ren, B., H. Cam, Y. Takahashi, T. Volkert, J. Terragni, R. A. Young, and B. D. Dynlacht. 2002. E2F integrates cell cycle progression with DNA repair, replication, and G(2)/M checkpoints. Genes Dev. 16:245-256.

37. Rogakou, E. P., D. R. Pilch, A. H. Orr, V. S. Ivanova, and W. M. Bonner. 1998. DNA double-stranded breaks induce histone H2AX phosphorylation on serine 139. J. Biol. Chem. 273:5858-5868.

38. Rogel, M. E., L. I. Wu, and M. Emerman. 1995. The human immunodeficiency virus type 1 vpr gene prevents cell proliferation during chronic infection. J. Virol. 69:882-888.

39. Rogoff, H. A., M. T. Pickering, M. E. Debatis, S. Jones, and T. F. Kowalik. 2002. E2F1 induces phosphorylation of p53 that is coincident with p53 accumulation and apoptosis. Mol. Cell. Biol. 22:5308-5318.

40. Roshal, M., B. Kim, Y. Zhu, P. Nghiem, and V. Planelles. 2003. Activation of ATR-mediated DNA damage response by the HIV-1 viral protein R. J. Biol. Chem. 278:25879-25886.

41. Shostak, L. D., J. Ludlow, J. Fisk, S. Pursell, B. J. Rimel, D. Nguyen, J. D. Rosenblatt, and V. Planelles. 1999. Roles of p53 and caspases in the induction of cell cycle arrest and apoptosis by HIV-1 vpr. Exp. Cell Res. 251:156-165.

42. Smits, V. A., R. Klompmaker, L. Arnaud, G. Rijksen, E. A. Nigg, and R. H. Medema. 2000. Polo-like kinase-1 is a target of the DNA damage checkpoint. Nat. Cell Biol. 2:672-676.

43. Somasundaran, M., M. Sharkey, B. Brichacek, K. Luzuriaga, M. Emerman, J. L. Sullivan, and M. Stevenson. 2002. Evidence for a cytopathogenicity determinant in HIV-1 Vpr. Proc. Natl. Acad. Sci. USA 99:9503-9508.

44. Taylor, J. R., Jr., K. C. Kimbrell, R. Scoggins, M. Delaney, L. Wu, and D. Camerini. 2001. Expression and function of chemokine receptors on human thymocytes: implications for infection by human immunodeficiency virus type 1. J. Virol. 75:8752-8760.

45. Tibbetts, R. S., D. Cortez, K. M. Brumbaugh, R. Scully, D. Livingston, S. J. Elledge, and R. T. Abraham. 2000. Functional interactions between BRCA1 and the checkpoint kinase ATR during genotoxic stress. Genes Dev. 14:2989-3002.
46. Ward, I. M., and J. Chen. 2001. Histone H2AX is phosphorylated in an ATR-dependent manner in response to replicational stress. J. Biol. Chem. 276:47759-47762.
47. Ward, I. M., K. Minn, and J. Chen. 2004. UV-induced ATR activation requires replication stress. J. Biol. Chem. 279: 9677-9680.
48. Ward, I. M., K. Mimi, K. G. Jorda, and J. Chen. 2003. Accumulation of checkpoint protein 53BP1 at DNA breaks involves its binding to phosphorylated histone H2AX. J. Biol. Chem. 278:19579-19582.
49. Weiss, R. S., T. Enoch, and P. Leder. 2000. Inactivation of mouse Hus1 results in genomic instability and impaired responses to genotoxic stress. Genes Dev. 14:1886-1898.
50. Wolf, D., V. Witte, B. Laffert, K. Blume, E. Stromer, S. Trapp, P. d'Aloja, A. Schurmann, and A. S. Baur. 2001. HIV-1 Nef associated PAK and PI3-kinases stimulate Akt-independent Bad-phosphorylation to induce anti-apoptotic signals. Nat. Med. 7:1217-1224.
51. Yang, J., Z. P. Xu, Y. Huang, H. E. Hamrick, P. J. Duerksen-Hughes, and Y. N. Yu. 2004. ATM and ATR: sensing DNA damage. World J. Gastroenterol. 10:155-160.
52. Zhang, S., D. Pointer, G. Singer, Y. Feng, K. Park, and L. J. Zhao. 1998. Direct binding to nucleic acids by Vpr of human immunodeficiency virus type 1. Gene 212:157-166.
53. Zhu, Y., H. A. Gelbard, M. Roshal, S. Pursell, B. D. Jamieson, and V. Planelles. 2001. Comparison of cell cycle arrest, transactivation, and apoptosis induced by the simian immunodeficiency virus SIVagm and human immunodeficiency virus type 1 vpr genes. J. Virol. 75:3791-3801.
54. Zou, L., D. Cortez, and S. J. Elledge. 2002. Regulation of ATR substrate selection by Rad17-dependent loading of Rad9 complexes onto chromatin. Genes Dev. 16:198-208.
55. Zou, L., and S. J. Elledge. 2003. Sensing DNA damage through ATRIP recognition of RPA-ssDNA complexes. Science 300:1542-1548.
56. Bernstein C, Bernstein H, Payne C M and Garewal H (2002) DNA repair/pro-apoptotic dual-role proteins in five major DNA repair pathways: fail-safe protection against carcinogenesis. Mutat Res. 511:145-178.
57. Chen I T, Smith M L, O'Connor P M and Fornace A J, Jr. (1995) Direct interaction of Gadd45 with PCNA and evidence for competitive interaction of Gadd45 and p21Waf1/Cip1 with PCNA. Oncogene. 11:1931-1937.
58. Cortez D, Wang Y, Qin J and Elledge S J (1999) Requirement of ATM-dependent phosphorylation of brca1 in the DNA damage response to double-strand breaks. Science. 286:1162-1166.
59. Fauci A S (1988) The human immunodeficiency virus: infectivity and mechanisms of pathogenesis. Science. 239: 617-622.
60. Foray N, Marot D, Gabriel A, Randrianarison V, Carr A M, Perricaudet M, Ashworth A and Jeggo P (2003) A subset of ATM- and ATR-dependent phosphorylation events requires the BRCA1 protein. Embo J. 22:2860-2871.
61. Fornace A J, Jr., Alamo I, Jr. and Hollander M C (1988) DNA damage-inducible transcripts in mammalian cells. Proc Natl Acad Sci USA. 85:8800-8804.
62. Gandhi R T, Chen B K, Straus S E, Dale J K, Lenardo M J and Baltimore D (1998) HIV-1 directly kills CD4$^+$ T cells by a Fas-independent mechanism. J Exp Med. 187: 1113-1122.
63. Gatei M, Zhou B B, Hobson K, Scott S, Young D and Khanna K K (2001) Ataxia telangiectasia mutated (ATM) kinase and ATM and Rad3 related kinase mediate phosphorylation of Brca1 at distinct and overlapping sites. In vivo assessment using phosphospecific antibodies. J Biol. Chem. 276:17276-17280.
64. Gaynor E M and Chen I S (2001) Analysis of Apoptosis Induced by HIV-1 Vpr and Examination of the Possible Role of the hHR23A Protein. Exp Cell Res. 267:243-257.
65. Harkin D P, Bean J M, Miklos D, Song Y H, Truong V B, Englert C, Christians F C, Ellisen L W, Maheswaran S, Oliner J D and Haber D A (1999) Induction of GADD45 and JNK/SAPK-dependent apoptosis following inducible expression of BRCA1. Cell. 97: 575-586.
66. Hazenberg M D, Hamann D, Schuitemaker H and Miedema F (2000) T cell depletion in HIV-1 infection: how CD4+ T cells go out of stock. Nat Immunol. 1:285-289.
67. Jacotot E, Ravagnan L, Loeffler M, Ferri K F, Vieira H L, Zamzami N, Costantini P, Druillennec S, Hoebeke J, Briand J P, Irinopoulou T, Daugas E, Susin S A, Cointe D, Xie Z H, Reed J C, Roques B P and Kroemer G (2000) The HIV-1 viral protein R induces apoptosis via a direct effect on the mitochondrial permeability transition pore. J Exp Med. 191: 33-46.
68. Jin S, Antinore M J, Lung F D, Dong X, Zhao H, Fan F, Colchagie A B, Blanck P, Roller P P, Fornace A J, Jr. and Zhan Q (2000) The GADD45 inhibition of Cdc2 kinase correlates with GADD45-mediated growth suppression. J Biol. Chem. 275:16602-16608.
69. Kastan M B, Zhan Q, el-Deiry W S, Carrier F, Jacks T, Walsh W V, Plunkett B S, Vogelstein B and Fornace A J, Jr. (1992) A mammalian cell cycle checkpoint pathway utilizing p53 and GADD45 is defective in ataxia-telangiectasia. Cell. 71:587-597.
70. Kearsey J M, Coates P J, Prescott A R, Warbrick E and Hall P A (1995) Gadd45 is a nuclear cell cycle regulated protein which interacts with p21Cip1. Oncogene. 11:1675-1683.
71. MacLachlan T K, Somasundaram K, Sgagias M, Shifinan Y, Muschel R J, Cowan K H and El-Deiry W S (2000) BRCA1 effects on the cell cycle and the DNA damage response are linked to altered gene expression. J Biol Chem. 275:2777-2785.
72. MacLachlan T K, Takimoto R and El-Deiry W S (2002) BRCA1 directs a selective p53-dependent transcriptional response towards growth arrest and DNA repair targets. Mol Cell Biol. 22:4280-4292.
73. Mita H, Tsutsui J, Takekawa M, Witten E A and Saito H (2002) Regulation of MTK1/MEKK4 kinase activity by its N-terminal autoinhibitory domain and GADD45 binding. Mol Cell Biol. 22:4544-4555.
74. Muthumani K, Hwang D S, Desai B M, Zhang D, Dayes N, Green D R and Weiner D B (2002) HIV-1 Vpr induces apoptosis through caspase 9 in T cells and peripheral blood mononuclear cells. J Biol Chem. 277: 37820-37831.
75. Nishizawa M, Kamata M, Mojin T, Nakai Y and Aida Y (2000) Induction of apoptosis by the Vpr protein of human immunodeficiency virus type 1 occurs independently of G(2) arrest of the cell cycle. Virology. 276:16-26.
76. O'Doherty U, Swiggard W J and Malim M H (2000) Human immunodeficiency virus type 1 spinoculation enhances infection through virus binding. *J Virol.* 74:10074-10080.
77. Oh-Hashi K, Maruyama W and Isobe K (2001) Peroxynitrite induces GADD34, 45, and 153 VIA p38 MAPK in human neuroblastoma SH-SY5Y cells. Free Radic Biol Med. 30:213-221.
78. Papathanasiou M A, Kerr N C, Robbins J H, McBride O W, Alamo I, Jr., Barrett S F, Hickson I D and Fornace A J, Jr. (1991) Induction by ionizing radiation of the gadd45 gene in cultured human cells: lack of mediation by protein kinase C. Mol Cell Biol. 11:1009-1016.
79. Roshal M, Zhu Y and Planelles V (2001) Apoptosis in AIDS. Apoptosis. 6:103-116.
80. Sampath D, Rao V A and Plunkett W (2003) Mechanisms of apoptosis induction by nucleoside analogs. Oncogene. 22:9063-9074.
81. Scully R and Livingston D M (2000) hi search of the tumour-suppressor functions of BRCA1 and BRCA2. Nature. 408: 429-432.
82. Shaw G M, Hahn B H, Arya S K, Groopman J E, Gallo R C and Wong-Staal F (1984) Molecular characterization of human T-cell leukemia (lymphotropic) virus type III in the acquired immune deficiency syndrome. Science. 226: 1165-1171.

the mitochondrial inner membrane during apoptosis: impact of the adenine nucleotide translocator. Cell Death Differ. 7: 1146-1154.
89. Waldhuber M G, Bateson M, Tan J, Greenway A L and McPhee D A (2003) Studies with GFP-Vpr fusion proteins: induction of apoptosis but ablation of cell-cycle arrest despite nuclear membrane or nuclear localization. Virology. 313:91-104.
90. Wang X, Gorospe M and Holbrook N J (1999) gadd45 is not required for activation of c-Jun N-terminal kinase or p38 during acute stress. J Biol Chem. 274:29599-29602.
91. Xu X, Weaver Z, Linike S P, Li C, Gotay J, Wang X W, Harris C C, Ried T and Deng C X (1999) Centrosome amplification and a defective G2-M cell cycle checkpoint induce genetic instability in BRCA1 exon 11 isoform-deficient cells. Mol Cell. 3: 389-395.
92. Yamane K, Wu X and Chen J (2002) A DNA damage-regulated BRCT-containing protein, TopBP1, is required for cell survival. Mol Cell Biol. 22:555-566.87.
93. Zagury D, Bernard J, Leonard R, Cheynier R, Feldman M, Sarin P S and Gallo R C (1986) Long-term cultures of HTLV-III-infected T cells: a model of cytopathology of T-cell depletion in AIDS. Science. 231: 850-853.64.
94. Zhan Q, Antinore M J, Wang X W, Carrier F, Smith M L, Harris C C and Fornace A J, Jr. (1999) Association with Cdc2 and inhibition of Cdc2/Cyclin B1 kinase activity by the p53-regulated protein Gadd45. Oncogene. 18:2892-2900.82.

```
SEQUENCE LISTING

<160> NUMBER OF SEQ ID NOS: 1

<210> SEQ ID NO 1
<211> LENGTH: 9
<212> TYPE: PRT
<213> ORGANISM: Artificial
<220> FEATURE:
<223> OTHER INFORMATION: targeting peptide for adipose tissue

<400> SEQUENCE: 1

Cys Lys Gly Gly Arg Ala Lys Asp Cys
1               5
```

83. Smith M L, Chen I T, Zhan Q, Bae I, Chen C Y, Gilmer T M, Kastan M B, O'Connor P M and Fornace A J, Jr. (1994) Interaction of the p53-regulated protein Gadd45 with proliferating cell nuclear antigen. Science. 266:1376-1380.
84. Soldani C, Bottone M G, Pellicciari C and Scovassi A I (2001) Two-color fluorescence detection of Poly (ADP-Ribose) Polymerase-1 (PARP-1) cleavage and DNA strand breaks in etoposide-induced apoptotic cells. Eur J Histochem. 45:389-392.
85. Soldani C, Lazze M C, Bottone M G, Tognon G, Biggiogera M, Pellicciari C E and Scovassi A I (2001) Poly (ADP-ribose) polymerase cleavage during apoptosis: when and where? Exp Cell Res. 269:193-201.
86. Stewart S A, Poon B, Jowett J B and Chen I S (1997) Human immunodeficiency virus type 1 Vpr induces apoptosis following cell cycle arrest. J. Virol. 71: 5579-5592.
87. Stewart S A, Poon B, Jowett J B, Xie Y and Chen I S (1999) Lentiviral delivery of HIV-1 Vpr protein induces apoptosis in transformed cells. Proc Natl Acad Sci USA. 96: 12039-12043.
88. Vieira H L, Haouzi D, El Hamel C, Jacotot E, Belzacq A S, Brenner C and Kroemer G (2000) Permeabilization of

What is claimed is:
1. A method of inducing apoptosis in a cancer cell, the method comprising:
introducing HIV-1 Viral protein R (Vpr) and Breast Cancer-Associated Protein I (BRCA1) to a cancer cell; and
inducing apoptosis in the cancer cell; wherein the cancer cell has been identified as lacking a functional BRCA1 gene.
2. The method according to claim 1, wherein the cancer cell is in a subject.
3. The method according to claim 2, wherein the subject is a mammal.
4. The method according to claim 1, wherein the cancer cell comprises a cell culture system.
5. A method of treating a cancer in a subject comprising conducting on the subject the method of claim 2.
6. The method of claim 5, wherein the cancer is breast cancer.
7. The method of claim 1, wherein the Vpr and BRCA1 are expressed by an expression vector.

* * * * *